US009567632B2

(12) United States Patent
Richard

(10) Patent No.: US 9,567,632 B2
(45) Date of Patent: *Feb. 14, 2017

(54) ENRICHMENT OF TARGET SEQUENCES

(71) Applicant: New England Biolabs, Inc., Ipswich, MA (US)

(72) Inventor: Cynthia L. Richard, Essex, MA (US)

(73) Assignee: New England Biolabs, Inc., Ipswich, MA (US)

(*) Notice: Subject to any disclaimer, the term of this patent is extended or adjusted under 35 U.S.C. 154(b) by 64 days.

This patent is subject to a terminal disclaimer.

(21) Appl. No.: 14/219,542

(22) Filed: Mar. 19, 2014

(65) Prior Publication Data

US 2014/0287468 A1    Sep. 25, 2014

Related U.S. Application Data

(60) Provisional application No. 61/803,246, filed on Mar. 19, 2013.

(51) Int. Cl.
*C12Q 1/68* (2006.01)
*C12P 19/34* (2006.01)
(Continued)

(52) U.S. Cl.
CPC ........... *C12Q 1/6874* (2013.01); *C12Q 1/6806* (2013.01); *C12Q 1/6888* (2013.01); *C12Q 2600/16* (2013.01)

(58) Field of Classification Search
USPC ............ 435/6.1, 6.11, 6.12, 91.1, 91.2, 91.51,435/183; 436/94, 501; 536/23.1, 24.3, 24.33, 536/25.3
See application file for complete search history.

(56) References Cited

U.S. PATENT DOCUMENTS 9,315,807 B1 *  4/2016  Richard ............ C12N 15/1072
2003/0096232 A1   5/2003  Kris et al.
(Continued)

FOREIGN PATENT DOCUMENTS

WO    WO 97/47640    12/1997
WO    WO 99/36571    7/1999
(Continued)

OTHER PUBLICATIONS

Bourzac, et al., Journal of Biotechnology, 154, 68-75 (2011).
(Continued)

*Primary Examiner* — Frank Lu
(74) *Attorney, Agent, or Firm* — New England Biolabs, Inc; Harriet M. Strimpel

(57) ABSTRACT

Methods and compositions are provided for enriching for target sequences from a population of nucleic acids, that includes combining in solution, a population of nucleic acids and a target isolation probe wherein the target isolation probe includes an affinity binding domain; permitting a single stranded region of the target isolation probe to hybridize to all or a portion of a target sequence in the population of nucleic acids; selectively immobilizing the hybridized nucleic acids from the population containing the target sequences by associating the target isolation probe with a capture domain and removing unbound material; and removing from the 3' end of the target sequence, a non-target sequence by means of one or more 3' single strand specific exonucleases. Target enrichment may be used to detect variations in nucleotide sequence for detecting phenotypic changes related to health or disease.

36 Claims, 9 Drawing Sheets

(51) Int. Cl.
*C07H 21/02* (2006.01)
*C07H 21/04* (2006.01)
*C07H 21/00* (2006.01)

(56) References Cited

U.S. PATENT DOCUMENTS

| | | | |
|---|---|---|---|
| 2006/0068417 A1* | 3/2006 | Becker | C12Q 1/6834 435/6.11 |
| 2007/0269825 A1* | 11/2007 | Wang | C12Q 1/6858 435/5 |
| 2008/0050735 A1 | 2/2008 | Pushnova | |
| 2012/0164754 A1* | 6/2012 | Rhee | G01N 33/5308 436/501 |
| 2013/0296194 A1* | 11/2013 | Jacobson | C12N 15/10 506/16 |

FOREIGN PATENT DOCUMENTS

WO    WO 02/16647    8/2002
WO    WO 2011/056863    5/2011

OTHER PUBLICATIONS

Okou, et al., Nature Methods, 4, 11, 907-909 (2007).
International Search Report and Written Opinion of the International Searching Authority for Application No. PCT/US2014/031222 dated Jul. 18, 2014.

* cited by examiner

ENRICHMENT OF TARGET SEQUENCES

CROSS REFERENCE

This application claims priority from U.S. provisional application Ser. No. 61/803,246 filed Mar. 19, 2013, herein incorporated by reference.

BACKGROUND

Next Generation Sequencing (NGS) has proved to be an invaluable tool in the diagnosis and treatment of numerous diseases, including cancer (Dancey, et al. *Cell*, 48:409-420 (2012); Dawson, et al. *NEJM*, 368:1199-1209 (2013)), cardiomyopathy (Meder, et al. *Circ. Cardiovasc. Genet.*, 4:110-122 (2011); Norton, et al. *Curr. Opin. Cariol.*, 27:214-20 (2012)), inherited disorders (Boycott, et al. *Nature Genetics*, 14:681-691 (2013)), prenatal screening (Nepomnyashchaya, et al. *Clin Chem Lab Med.*, 51:1141-54 (2013); Papgeorgiou, et al. *Genome Medicine*, 4:46 (2012)), and neurological disorders (Nemeth, et al. *Brain*, 136:3106-180 (2013)). However, although NGS enables the sequencing of entire human genomes within days, the cost of sequencing and the burden of data analysis severely inhibit the translation of whole genome sequencing to the clinic. As a result, enrichment of target sequences is desirable to facilitate molecular diagnostics that rely on NGS (Agilent, (Santa Clara, Calif.), Roche/NimbleGen (Madison, Wis.), Illumina (San Diego, Calif.), Life Technologies (Grand Island, N.Y.)), multiplex PCR (Life Technologies, Illumina, Qiagen (Valencia, Calif.), Kailos Genetics (Huntsville, Ala.)), molecular inversion probes (Hiatt, et al. *Genome Res.*, 23, 843-54 (2013)), highly-parallel PCR (Fluidigm (San Francisco, Calif.), Raindance (Billerica, Mass.)), and single primer amplification methods (Enzymatics/ArcherDx (Beverly, Mass.), NuGen (San Carlos, Calif.)).

Current methods for enrichment include hybridization capture from prepared DNA libraries (Albert, et al. *Nature Methods*, 4:903-905 (2007); Okou, et al. *Nature Methods*, 4:907-909 (2007)). Hybridization capture requires an array of immobilized probes. In theory, fragmented nucleic acids in solution hybridize to these immobilized probes if they have complementary sequence. These methods have the same disadvantages as for solution hybridization with the exception that both strands of a duplex can be captured. However additional disadvantages of these methods include reduced efficiency of hybridization when the probes are bound to a surface prior to hybridization. Additional disadvantages include lengthy 2-3 day protocol, multiple steps which increase the cost of the tests, a requirement for large amounts of initial input DNA (1 µg-5 µg); broad library size distribution, only 55%-65% specificity, 80%+/−200-500 base-pair (bp), and an inability to capture repeats or to handle nucleic acids containing repeat sequences within non-target sequences.

Current methods are not suited for specifying read start sites (the position at which sequencing of nucleic acid molecules begins) because of the reliance on artificial sequence at the ends of the targets. Moreover current methods are not suited for capturing both target strands. Present hybridization methods typically capture nucleic acid fragments greater than the average size of on exons, which is less than 200 bp as described by Sakharkar, et al. *In Silico Biology*, 4:387-393 (2004), resulting in substantially non-target sequencing, due to the inability to specifically define the read start sites. Performance comparison of hybridization-based exome capture technologies has been reviewed by Clark, et al. *Nature Biotechnology*, 29:908-914 (2011).

Multiplex PCR is an alternative to capture hybridization. Multiplex PCR methods are considerably faster and do not require library preparation prior to enrichment, but there is limited scalability per reaction due to primer interactions, variable uniformity of amplification across targets due to amplification bias that arises from the use of sets of primers that amplify with different efficiencies, an inability to filter duplicates, and the addition of primer sequences used to anneal to the targets are included on the ends of the amplicons. These sequences must be read through during sequencing, thereby increasing sequencing time and cost. Moreover, the sequence of the synthetic primers is contained in the sequence report in addition to target sequence generating unnecessary sequence complexity. Both molecular inversion probes and highly-parallel PCR resolve some of the issues encountered by multiplex PCR, but both methods are significantly more expensive. Molecular inversion probes require the synthesis on long oligonucleotides and there are equipment costs associated with highly-parallel PCR methods. In addition, both methods also introduce synthetic primer sequences on the ends of the amplicons. Single primer methods introduce primer sequences at only one end of the amplicon, reducing the amount of primer sequenced in half, but sacrifice the additional selectivity applied by using two primers to enrich the correct target sequence. As a result, the need remains for a method of target enrichment that minimizes the sequencing of off-target or primer regions with high scalability, specificity, and uniformity.

SUMMARY

In general, methods and compositions are provided for enriching for target sequences from a population of nucleic acids. The method includes: combining in solution, a population of nucleic acids and a target isolation probe wherein the target isolation probe comprises an affinity binding domain; permitting a single stranded region of the target isolation probe to hybridize to all or a portion of a target sequence in the population of nucleic acids; selectively immobilizing the hybridized nucleic acids from the population containing the target sequences by associating the target isolation probe with a capture domain and removing unbound material; and removing from the 3' end of the target sequence, a non-target sequence by means of one or more 3' single strand specific exonucleases.

In various aspects, some or all of the nucleic acids in the population contains a repeat sequence, and the population of nucleic acids may be combined with a removable blocking oligonucleotide that hybridizes to the repeat sequence before or together with the target isolation probe. It may be advantageous to use an excess of the removable blocking oligonucleotide and to permit hybridization after a duplex denaturation step. The removable blocking oligonucleotide in the nucleic acid/removable oligonucleotide duplex may then be selectively degraded at the same time or prior to degradation of 3' non-target sequences with 3' single strand specific exonuclease(s). Degrading the removable blocking oligonucleotide may be accomplished by an RNAse if the removable blocking oligonucleotide is RNA or by uracil deglycosylase and endonuclease if for example, the removable blocking oligonucleotide is DNA containing a plurality of uracils or by any other suitable technique for specifically cleaving the removable blocking oligonucleotide.

In various aspects, the single stranded region of the target isolation probe described above may hybridize to both the 3' end and the 5' end of the target sequence. In these circumstances an affinity domain is preferably associated with the target isolation probe at a site located between but not at the 3' end or 5' end of the target isolation probe. Hybridization with a target sequence may occur along the length of the target isolation probe under the moderately stringent conditions of hybridization. These conditions may permit individual base pair mismatches to occur as might be expected if the use of the methods is to detect single nucleotide polymorphisms. Alternatively, hybridization may occur at the ends of the target isolation probe with significant internal regions of mismatch that might arise due to insertions or deletions that might characterize the selected target sequences from different sources. Once the target sequence/target isolation probe is immobilized by association of the affinity domain with an immobilized capture domain and after the 3' non-target sequence has been removed or at the same time of removal using one or more 3' exonucleases, the 5' non-target sequence may be removed from the 5' end of the target sequence, by means of one or more 5' single strand specific exonucleases. Subsequent to exonuclease digestion at 3' and 5' ends of the target sequence, to generate a blunt or staggered end suitable for ligating an adaptor, the adaptors are ligated to the target sequence so that the target sequence may be readily identified, isolated, amplified, sequenced, characterized and/or analyzed for phenotypically significant sequence variations.

Aspects of the methods utilize different configurations of the target isolation probe and may be used in conjunction with a second probe described herein. Regardless of the probes, certain common features of the method are preserved namely hybridization of nucleic acids in a population with a target isolation probe associated with an affinity domain followed by a first step of enrichment that occurs when the target isolation probe is immobilized permitting non-hybridizing nucleic acids and reagents to be removed by washing and then removing 3' non-target sequences by exonuclease digestion.

In an aspect of the methods, the target isolation probe may be a flap probe, where the flap probe has a non-hybridizing double stranded region extending from the 3' end of the single stranded region. The non-hybridizing double stranded region may be ligated at the 5' end of one strand onto the 3' end of single strand region of the probe or may be part of the single strand probe to which a 3'-5' oligonucleotide is annealed that constitutes the second strand in the non-hybridizing double stranded region. Alternatively the non-hybridizing double stranded region may be formed from a hairpin at the 3' end of the single stranded probe that folds back and hybridizes with itself to form a double stranded region. Subsequent to hybridization of the flap probe to the 5' end of the target sequence, 5' non-target sequences can be removed by 5' flap endonuclease digestion and the 3'-5' oligonucleotide or hairpin may be ligated to the 5' end of the target sequence after a nicking step so as to serve as a 5' adaptor. A 3' adaptor may be ligated to the 3' end of the target sequence. The 3' and 5' adaptors may each contain one or more of a sequencing primer site, a library amplification primer site, a unique sample identifier and a unique molecule identifier sequence.

In another aspect of the methods, the single strand region of the target isolation probe hybridizes to a first portion of the target sequence. For example, an end of the target isolation probe forms a duplex with a sequence at or proximate to the 3' end or the 5' end of the target sequence. Hybridization is further permitted of a single stranded region of a second probe to a second portion of the target sequence at a position that is adjacent, proximate or distant from the target isolation probe where this position results in the second probe defining an end of the target sequence that is opposite to the target isolation probe. In one aspect, the second probe has a non-random sequence of no more than 90%, 70%, 50%, 30%, or 10% of the nucleotides in the target sequence and correspondingly wherein the target isolation sequence has a nucleotide sequence of no more than 10%, 30%, 50% or 70% or 90% of the target sequence.

In aspects of the methods, the affinity domain on a 3' target isolation probe may be positioned anywhere within or at the 3' end of the target isolation probe but excluding the 5' end whereas the affinity domain on a 5' target isolation probe may be positioned anywhere within or at the 5' end of the target isolation probe but excluding the 3' end.

In aspects of the methods, where the target isolation probe hybridizes to a portion of the target sequence for example at the 3' end of the target sequence, an oligonucleotide having a random sequence with a length in the range of 4-10 nucleotides may be used where this oligonucleotide serves as a primer for polymerase extension to create a double stranded 5' end suitable for adaptor ligation.

In another aspect of the methods, the target isolation probe or the second probe positioned in a 5' portion of the target sequence is a flap probe similar to that described above having a hybridizing single stranded region, and a non-hybridizing double stranded region extending from the 3' end of the single stranded region. A 5' non-target sequence may be removed by 5' exonuclease digestion to provide a blunt or staggered end suitable for adaptor ligation to the target sequence if a linear probe is used at the 5' end of the target sequence or a 5' flap endonuclease if a 5' flap probe is used. Blocking moieties for example, modified nucleotides are provided to prevent ligation of an adaptor to the target isolation probe or second probe. Where exonuclease digestion of the 5' end removes more or less than the 5' non-target sequence, an additional step of filling in the staggered end may be used prior to ligation of a 5' adaptor.

In any of the aspects of the methods described above, the 3' adaptor and optionally the 5' adaptor may be a hairpin adaptor. Use of a hairpin adaptor provides an additional advantage where the target isolation probe or second probe defining the end of the target sequence may be covalently linked to one end of the hairpin adaptor while the target sequence is covalently linked to the other end of the hairpin adaptor. Under denaturing conditions, a single stranded nucleic acid results with adaptor sequence available for initiating primed amplification of the target sequence.

In an aspect of the methods the 3' end of the target isolation sequence can be extended by means of a polymerase so as to displace the 5' probe after 5' exonuclease digestion.

In aspects of the methods, an adaptor is ligated to each end of the target sequence and the target sequence sequenced either directly or after amplification. The read start site in the sequencing reactions occurs at or proximate to the 3' end of the target sequence and is terminated at or proximate to the 5' end of the target sequence in a manner that permits sequencing of each nucleotide in the target sequence without concern of primers obscuring the target sequence or obscuring significant mutations in the target sequence. Examples of mutations include one or more of an insertion, deletion, or nucleotide polymorphism or single nucleotide polymorphism. In this way, correlations between mutations and phenotype of an organism can be faithfully recorded.

Because of removal of non-target sequences at one or both ends of the target sequence, unnecessary sequencing and analysis of non-target sequence is avoided. In general, a method is provided for analyzing an extract of an animal or plant that includes: obtaining a nucleic acid sample from the extract; enriching for target sequences as described above; and obtaining the nucleotide sequence of the enriched target molecules. In an aspect, the nucleotide sequence obtained from enriched target molecules comprises: fewer than 5 non-target nucleotides at the 3' end; or at least 90% of the target sequence. Prior to sequencing, the target sequences may be amplified using primer sequences that hybridize to sequences positioned within adaptors located at 3' and 5' ends of the target sequence. Once the target sequence is obtained, it may be used to establish a correlation of sequence changes with an altered phenotype from a prokaryote or eukaryote.

BRIEF DESCRIPTION OF THE FIGURES

FIG. 2A (7)-(11) follow from (1)-(3) in FIG. 1. (7) depicts a single stranded nucleic acid or one strand of a heat denatured random nucleic acid fragment to which a target isolation probe bearing an affinity domain has been attached and subsequently bound to a capture domain wherein the 3' non-target nucleic acid has been digested by one or more 3' single strand DNA exonucleases or RNA exonucleases leaving a 3' double-stranded blunt end. After digestion, the enzyme(s) and buffer are washed away; a 3' adaptor is then added to the 3' end (8). The structure of the adaptor is the same as described for (5). (9) depicts the product of digestion by one or more 5' single strand DNA exonuclease(s) or RNA exonuclease(s) leaving a double-stranded blunt end at the 5' end of the target nucleic acid or an end in which the target nucleic acid is either recessed or presents an overhang. After digestion, the enzyme(s) and buffer are washed away. If a portion of the target molecules contains staggered ends, the ends can be blunted by extension or digestion of the 3' end of the probe by a DNA polymerase, RNA polymerase or reverse transcriptase. Standard deoxynucleotides or ribonucleotides can be used for the extension or, a mixture containing one or more modified nucleotide triphosphates (NTPs), such as deoxyuracil triphosphate (dUTP), can be used to later digest any extended sequence. After blunting, the enzyme(s) and buffers are washed away. A 5' adaptor as described for (5) above is ligated to the 5' end of the target molecule (10) to enable PCR (11) as described for (6) above. The method shown in FIG. 2A can alternatively be performed by removing the 5' single stranded nucleic acid and ligation of the 5' adaptor first, followed by the removal of the 3' single stranded nucleic acid and ligation of the 3' adaptor.

FIG. 2B shows a variation on the method for target selection and enrichment depicted in FIG. 1. (12) follows from (1) which depicts a flap target isolation probe covalently linked to an affinity domain that is a flap probe where the 3' end of the target isolation probe contains a double stranded DNA region that is not complementary to the target and that contains part of or all of a NGS platform-specific adaptor sequence. This double stranded region can be created by hybridizing the 3' end of the single stranded region of the target isolation probe to a second oligonucleotide complementary to the NGS adaptor sequence before, during, or after hybridization of the target isolation probe to the target nucleic acid. Alternatively, the target isolation probe may form or be ligated to a hairpin with a cleavable site, generating a double stranded region spanning part or all of the adaptor sequence. The 3' end of the double stranded region terminates at the 3' end of the target isolation probe, or extends one or more bases past into the target isolation probe. The affinity domain may be located at any position within the target isolation probe, except at the 3' end of a hairpin probe. The molecule of (12) is immobilized on a capture domain (13). (14) shows the product of digestion of the 3' non-target nucleic acid followed by adaptor ligation which is achieved as described in FIG. 2A. The 5' single stranded DNA on the target molecule is cleaved by a flap endonuclease such as FEN-1, generating a nick between target nucleic acid and the double stranded region of the bait. The nick is ligated with a ligase such as T4 DNA ligase. (15) depicts the product of optional PCR of the target, as shown in FIG. 1.

FIG. 2C shows a variation of the method described in FIG. 1. A 3' adaptor (see for example the adaptor described in FIG. 1) which is unable to ligate to the target isolation probe is ligated to the 3' end of (4) to generate (16). (17) depicts the extension product of the 3' end of the adaptor by a DNA polymerase or reverse transcriptase having 3' exonuclease activity and capable of removing the ligation inhibiting modification such as a dideoxynucleotide and subsequently extending the 3' adaptor to form a blunt end and releasing the target from the immobilized target isolation probe. Standard deoxynucleotides or ribonucleotides can be used for the extension or, a mixture containing one or more modified NTPs, such as dUTP, can be used to later digest any extended sequence. After extension, the enzyme(s) and buffer are washed away. In (18), a 5' adaptor (see for example FIG. 1) is ligated to the 5' end of (17).

(28) is the product of (19)-(23) where a second probe is hybridized to the 5' portion of the target nucleic acid instead an oligonucleotide of 4-10 nucleotides having a random sequence. The 5' probe can include modifications on the 5' ends to prevent exonuclease degradation such as phosphorothioate linkages. In addition, internal modifications may be included to prevent amplification of the probes, such as one more dUs or one or more ribonucleotides. In (29) the 5' non-target nucleic acid has been removed by one or more 5' single strand DNA or RNA exonuclease(s) and followed by optional extension or digestion of the 3' end of the second probe. (30) depicts the addition of a 5' adaptor to (29). (31) corresponds to the amplification product of (30). In an alternative aspect, the method described in FIG. 4 can be performed first with hybridization of a 5' target isolation sequence containing an affinity domain at the 5' portion of the target nucleic acid followed by capture and removal of the unbound probe, 5' exonuclease digestion to remove 5' non-target sequences and ligation of the 5' adaptor prior to the hybridization of a 3' second probe to the 3' portion of the target nucleic acid and removal of non-target sequence with one or more 3' exonucleases.

Figure 4:
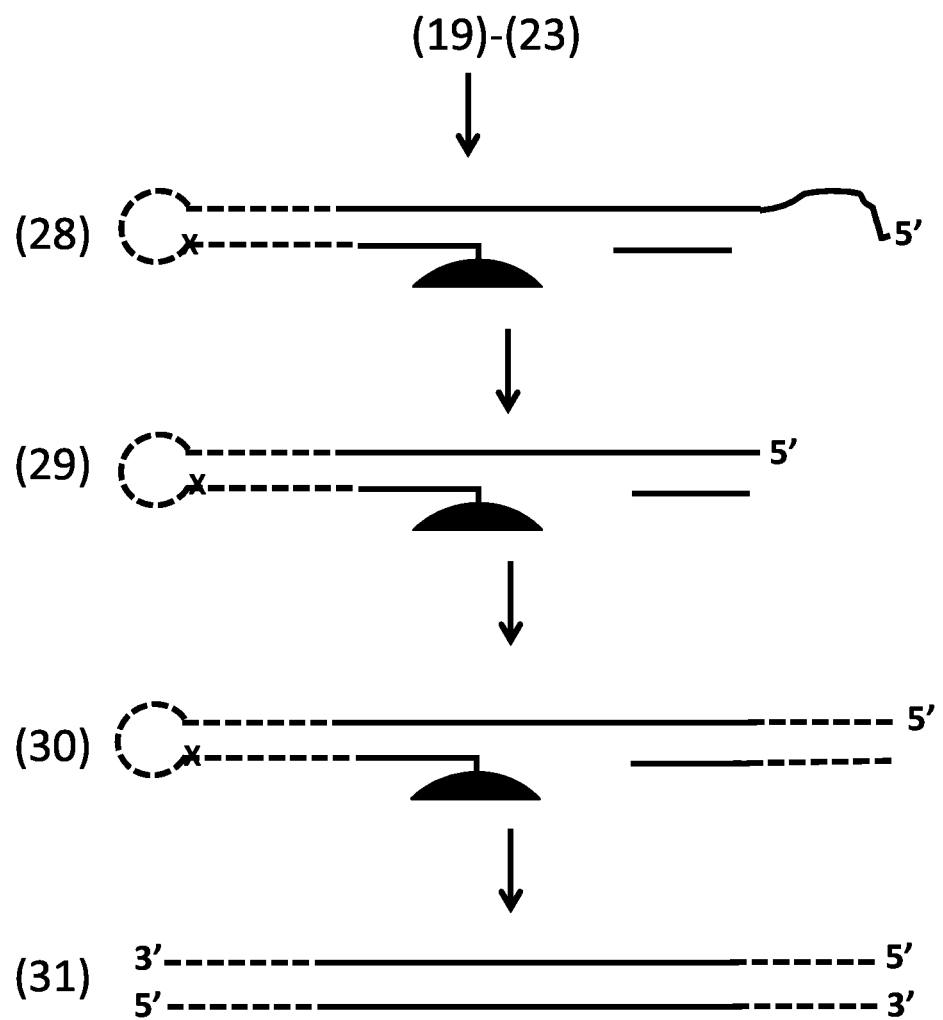
FIG. 4 shows a method for target isolation and enrichment that utilizes two probes where the second probe has a non-random sequence.
Figures 5A, 5B, 5C:
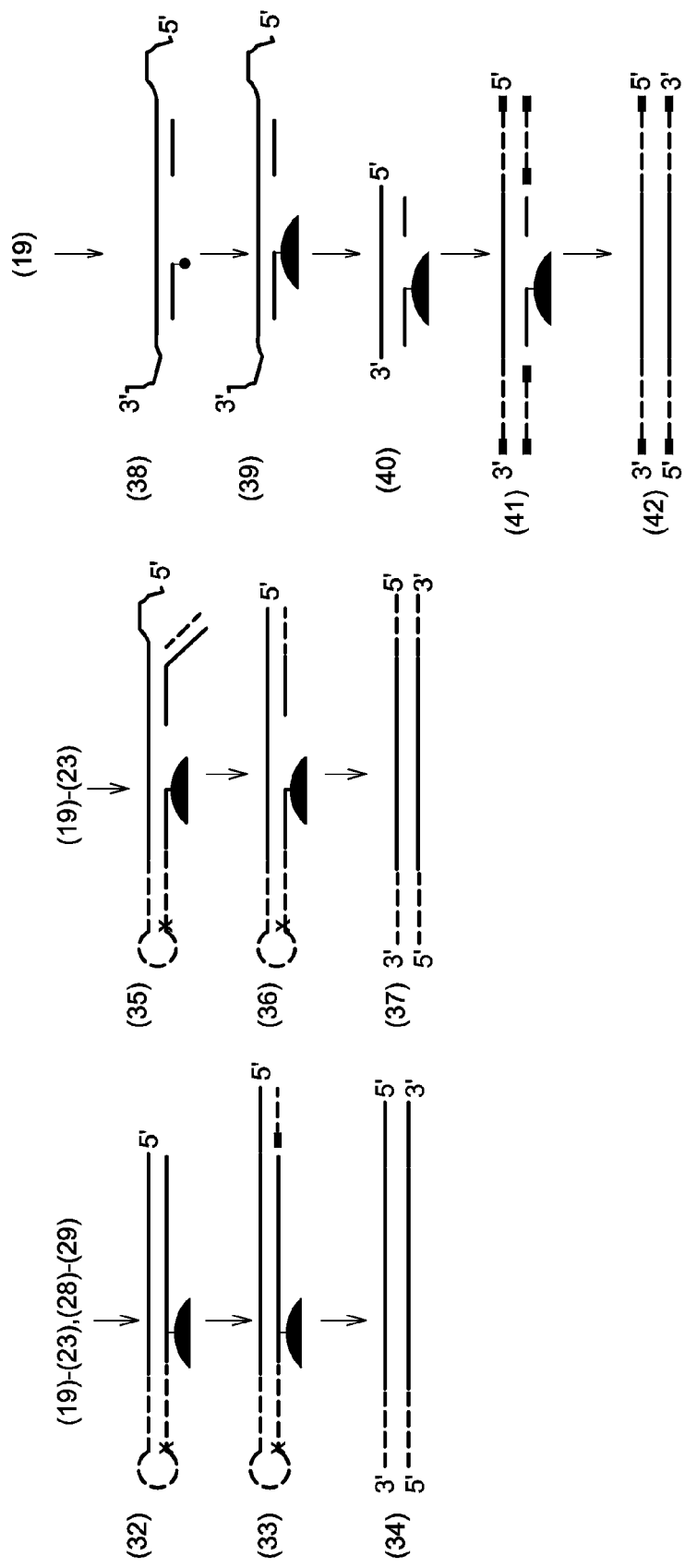

FIGS. 5A-C are variations of the two probe method described in FIG. 4.

FIG. 5A shows a method that is initiated by steps (19)-(23) followed by steps (28)-(29). (32) corresponds to target nucleic acid with an adaptor ligated to the 3' end of the target nucleic acid sequence. The target nucleic acid is hybridized to a 3' target isolation probe in which the affinity domain is covalently linked within the target isolation probe but not at the 3' or 5' end. The 3' target isolation probe can include modifications on the 3' and/or 5' ends to prevent exonuclease degradation, such as phosphorothioate linkages. Internal modifications may be included to prevent amplification of the target isolation probes, such as one more dUs or one or more ribonucleotides. (33) shows the product of extension of the 3' target isolation probe in (32) displacing the 5' probe and creating a blunt end to which a 5' adaptor is ligated. (34) shows the product of amplification.

FIG. 5B shows a variation on the method for target selection and enrichment involving two probes.

After steps (19)-(23), (35) corresponds to (23) to which a flap probe (described in FIG. 2B), without an affinity domain, is hybridized to the 5' end of the target region. (36) corresponds to (35) after cleavage of the 5' single stranded nucleic acid on the target molecule by a flap endonuclease such as FEN-1, generating a nick between target nucleic acid and the double stranded region of the probe. In (37) the nick in (36) is ligated with a ligase such as T4 DNA ligase. (37) is the product amplification of the target nucleic acid after elution.

Figure 2:
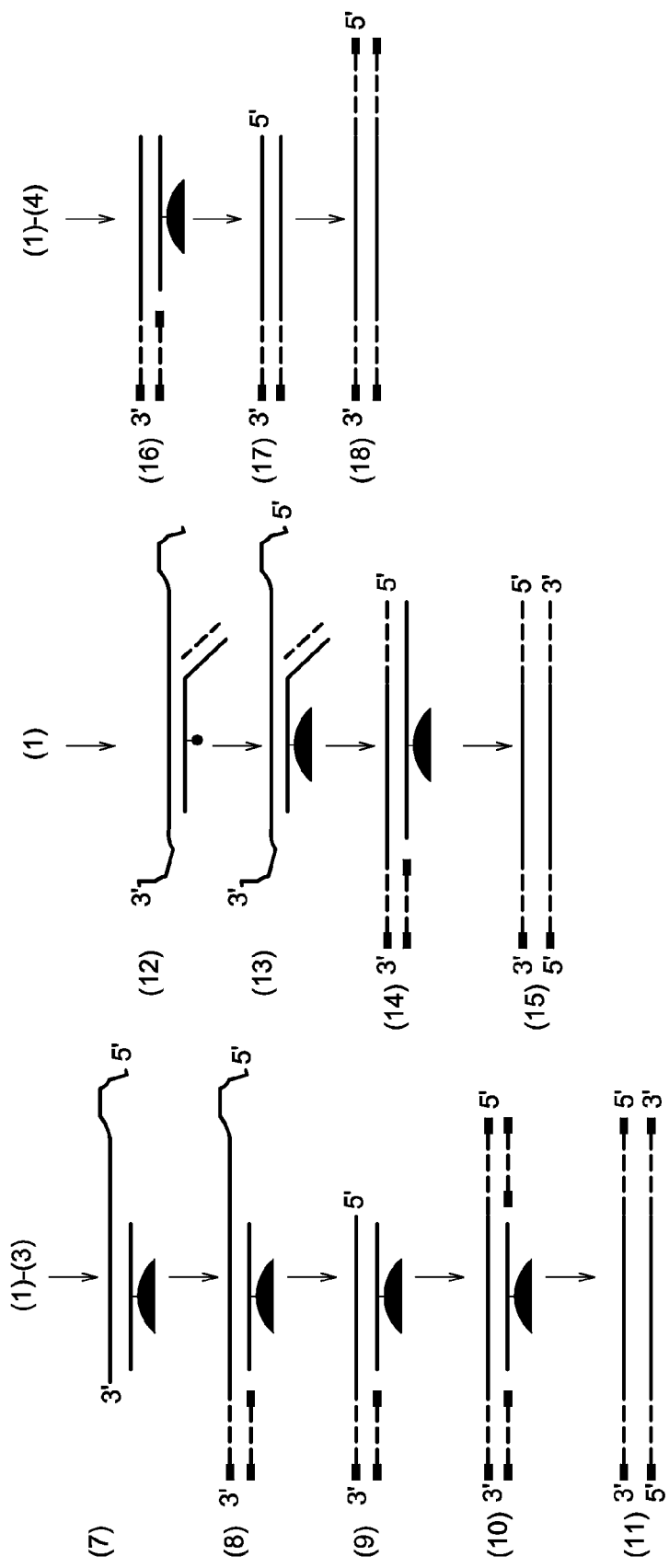
FIG. 2A-C shows variations on the method for target selection and enrichment described in FIG. 1.

A variation of the 5B includes hybridization of a 5' target isolation probe containing an affinity domain, as described in FIG. 2B, followed by capture and removal of the 5' single stranded nucleic acid by a flap endonuclease and ligation of the nick prior to the hybridization of a 3' target isolation probe lacking an affinity domain, removal of the 3' single stranded nucleic acid and ligation of the 3' adaptor.

FIG. 5C shows a variation on the method for target selection and enrichment involving two probes.

(38) is the product of (19) in which both the 3' target isolation probe containing an affinity domain and the 5' probe or both a 3' probe and a 5' target isolation probe containing an affinity domain are hybridized to the target nucleic acid sequence in a single reaction. In (39), the affinity binding domain on the target isolation sequence becomes bound to the capture domain immobilizing the target sequence. (40) is the product of digestion by 3' and 5' single strand DNA exonuclease(s) or RNA exonuclease(s) leaving a double-stranded blunt ends on both the 3' and 5' ends of the target nucleic acid/target isolation probe duplex. The 3' and 5' digestion can be performed together or in succession. After digestion, the enzyme(s) and buffers are washed away. (41) is (40) to which 3' and 5' adaptors have been added. (42) is the amplification product of (41).

FIG. 6A-D shows fragment analysis on an ABI sequencer which demonstrates the efficiency of 3' blunt ending.

Figure 6:
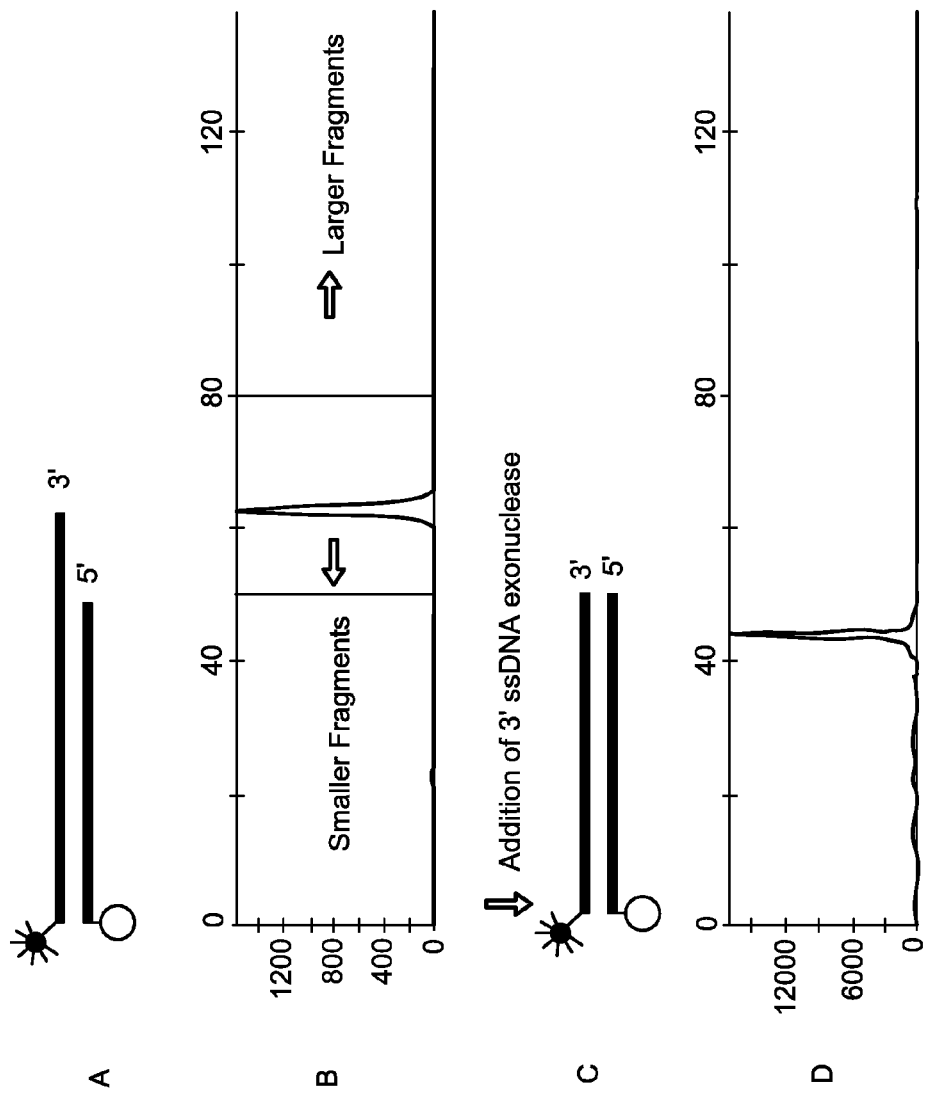

FIG. 6A shows schematically a 5'-FAM-labelled oligonucleotide hybridized to a 3'-biotinylated probe and bound to streptavidin beads, forming a 20 nt 3' overhang.

FIG. 6B shows the corresponding peak on a chromatogram from an ABI sequencer for fragment analysis.

FIG. 6C shows schematically the blunt ended 5'-FAM-labelled oligonucleotide after 3' ssDNA exonuclease treatment.

FIG. 6D shows a peak corresponding to FIG. 1C where the single peak correlates with the presence of blunt ended DNA.

FIG. 7A-D shows fragment analysis on an ABI sequencer which demonstrates the efficiency of 5' blunt ending using 3'-FAM labeled oligonucleotides. A 3'-FAM-labelled oligo is hybridized to a 5'-biotinylated probe and bound to streptavidin beads, forming a 20 nt 5' overhang. After incubation with 5' ssDNA exonuclease, followed by washing the beads to remove the enzyme, the FAM-labelled oligo is eluted in NaOH and run on an ABI sequencer for fragment analysis.

Figure 7:
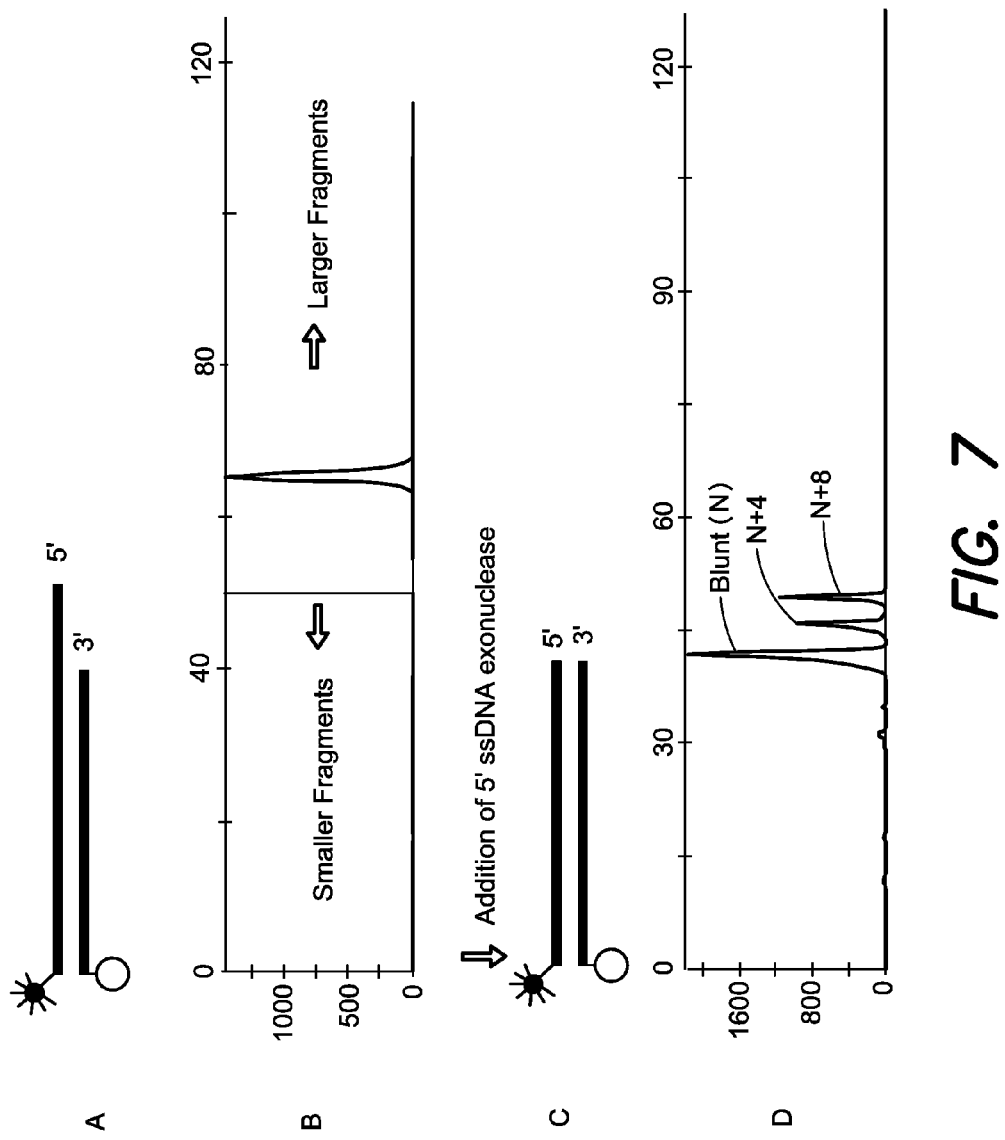

FIG. 7A and FIG. 7B show starting material.

FIG. 7C and FIG. 7D show the result of digestion of the overhang in which three peaks correlating to blunt dsDNA, 4-base overhangs, and 8-base overhangs are seen.

Figure 8:
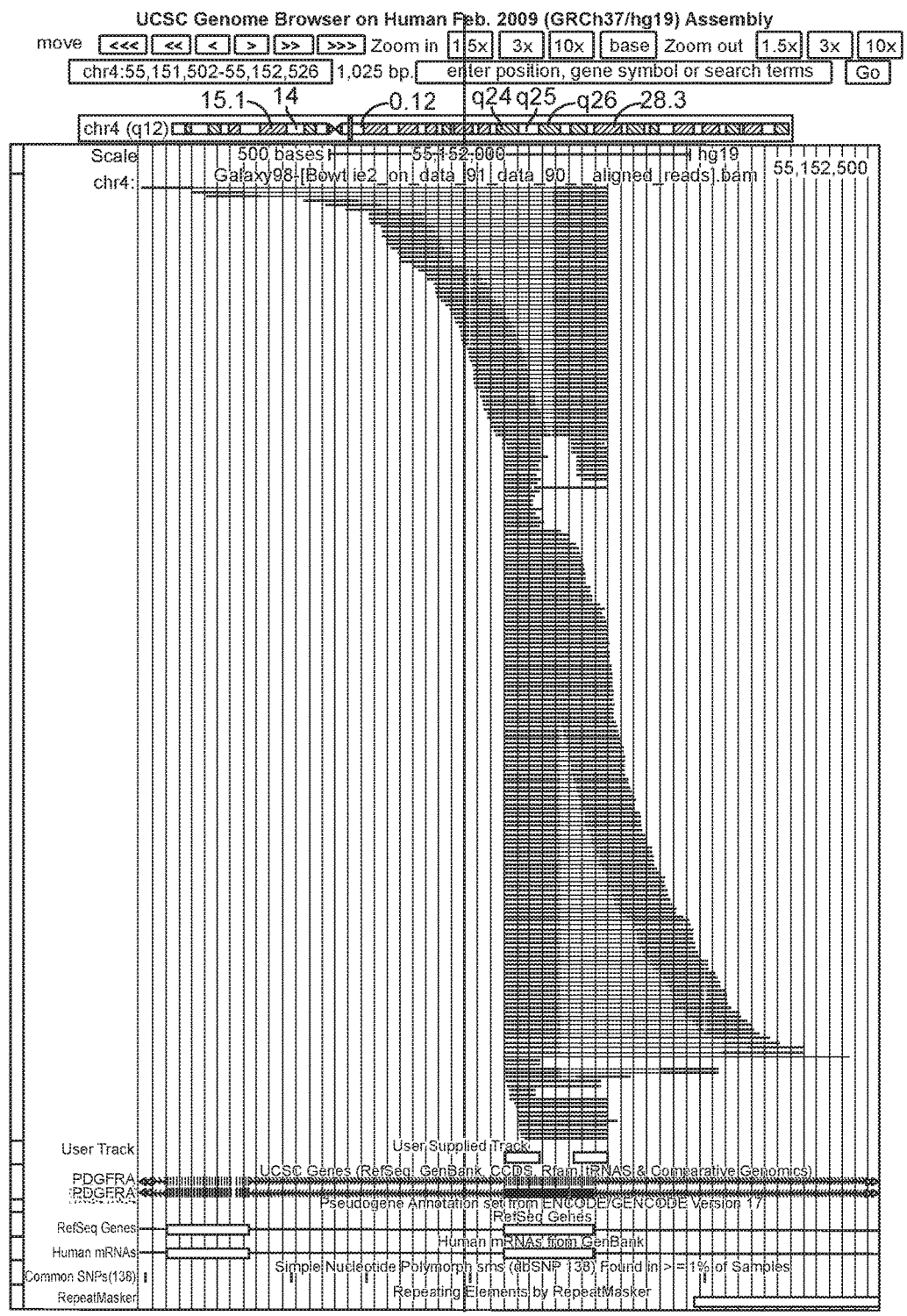

FIG. 8 shows capture of an exon in platelet-derived growth factor receptor alpha gene (PDGFRA). Biotinylated, target-specific probes were hybridized to sheared Jurkat genomic DNA (gDNA). The target sequences were captured by binding to streptavidin beads followed by washing in BW buffer. A 3' exonuclease was added to remove gDNA 3' of the probe, gDNA duplex, such that the 5' end of the probe defined the 3' end of the target. After 3' dA-tailing and adaptor ligation, a random primer was hybridized and extended to form a 5' blunt end, followed by ligation of the 5' adaptor. Library was amplified by PCR and sequenced on an Illumina MiSeq® system (Illumina, San Diego, CA). Shown is capture of PDGFRA target, with a fixed 3' end and random 5' end on the plus and minus strands.

Figure 9:
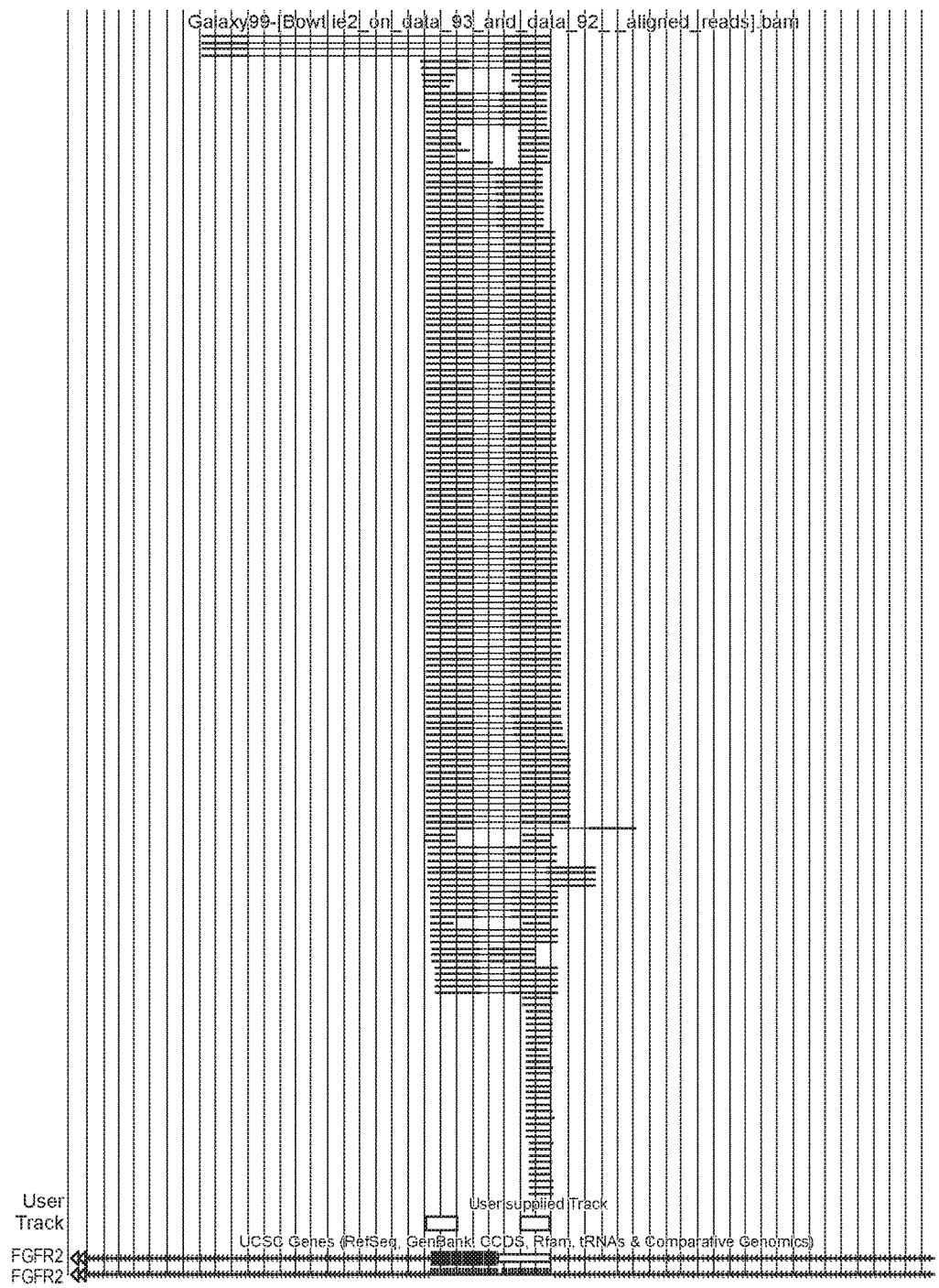

FIG. 9 shows capture of an exon in a fibroblast growth factor receptor gene (FGFR2). Biotinylated, target-specific probes were hybridized to sheared Jurkat gDNA. The targets were captured by binding to streptavidin beads followed by washing in Bind and Wash (BW) buffer. A 3' exonuclease was added to remove 3' non-target gDNA where the 5' end of the probe defined the 3' end of the target. After 3' dA-tailing and adaptor ligation, a target-specific 5' probe was hybridized to the target sequence and 5' ssDNA was digested by an exonuclease leaving either a blunt end or a small 5' overhang. The probes were extended by a DNA polymerase to form a blunt end, followed by ligation of the 5' adaptor. The target sequences were amplified by PCR and sequenced on an Illumina MiSeq. Captured of FGFR2 target sequences are shown with a fixed 3' and 5' end on the plus and minus strands.

DETAILED DESCRIPTION OF EMBODIMENTS

The methods and compositions described herein are not intended to be limited to the particular methodology, or reagents described herein unless specifically claimed but are provided as examples only. Several aspects are described below with reference to example applications for illustration. Where method steps involve standard well known methods to a person of ordinary skill in the art, these method steps are not described in detail. In this application, the use of the singular includes the plural unless specifically stated otherwise. "included," is not limiting and has an equivalent meaning to "comprising". The term "about" or "approximately" can mean within an acceptable error range for the particular value as determined by one of ordinary skill in the art, which will depend in part on how the value is measured or determined. Where particular values are described in the application and claims, the term "about" means within an acceptable error range for the particular value unless otherwise stated. The term "proximate" refers to a position that is adjacent or in the vicinity of a stated feature. For example, where "proximate" is used in the context of the position at which a probe hybridizes to a defined end of a target sequence, the term proximate may refer to less than 10 nucleotides from the stated feature. The term "distant" refers to a position that is not proximate to a stated feature but is positioned at a site that is more remote than would be the case if the position was proximate.

In general, methods are provided herein for enriching target nucleic acid sequences from a nucleic acid sample to create a target-enriched nucleic acid library. The term "target enrichment" with respect to a nucleic acid is intended to refer to increasing the relative concentration of particular nucleic acid species in the sample.

One or more of the following features can be achieved with enrichment methods described herein: analyzing both target strands of duplex nucleic acids to increase confidence in rare SNPs; ability to specify read start sites, generation of normalized probe pools regardless of GC content, the ability to target repeat regions, improved overall efficiency of detection of target sites, avoidance of loss of targets prior to capture, library preparation of targets independent of DNA damage outside of the target regions, reduced need for multiple probes to span a target region, capture of larger insertions and deletions (indels) between probe pairs, generation of libraries within a narrow size distribution for optimal clustering, reduction in the percentage of non-target bases contained in target sequences; minimization of required sequencing read length and required depth of coverage, increased uniformity and reduction in time and complexity for enrichment and library preparation compared with existing methods of hybridization-based target enrichment.

Nucleic acid that may have been purified but otherwise have not been treated or modified are referred to here as a nucleic acid sample. The nucleic acid sample may be optionally fragmented into a population of nucleic acids or nucleic acid molecules in a population from which target sequences or target molecules are enriched.

The term "nucleic acid sample" as used herein refers to DNA or RNA or a mixture of DNA and RNA molecules or sequences obtained from any source, containing target and non-target sequences. For example, a nucleic acid sample can be obtained from artificial sources or by chemical synthesis, or from viruses, prokaryotic cells including microbes, or eukaryotic cells. Biological samples may be vertebrate, including human or excluding humans, invertebrates, plants, microbes, viruses, mycoplasma, fungi or ancient. Biological fluids include blood, saliva, cerebral spinal fluid, pleural fluid, milk, lymph, sputum, semen, bone marrow, needle aspirates, and the like, solids (e.g., stool). Eukaryotic cell samples include embryonic tissue, biopsies or cadaver tissue, tissues, tissue culture, biopsies, organs, or other biological, agricultural or environmental sources. Cells can be first breached or broken apart either physically by using, for example, the use of small beads at high velocities, or chemically by using, for example, detergents and other surfactants to obtain the nucleic acid sample. An alcohol or other chemical can be used for precipitating the nucleic acid.

A nucleic acid sample may comprise whole genomic sequences, part of the genomic sequence, chromosomal sequences, chloroplast sequences, mitochondrial sequences, polymerase chain reaction (PCR) products, whole genome amplification products or products of other amplification protocols listed below under "amplification", cDNA sequences, mRNA sequences, non-coding RNA (ncRNA) or whole transcriptome sequences, exons, long terminal repeat regions (LTR), intron regions, and regulatory sequences. These examples are not to be construed as limiting the sample types applicable to aspects of the present invention.

A nucleic acid sample may give rise to a population of nucleic acids in which a subset of nucleic acid molecules in the population may contain target sequences for enrichment. The population of nucleic acids may be for example: the product of random cleavage using enzymatic, mechanical or chemical means; the product of non-random or biased cleavage which is generally achieved with enzymes such as restriction enzymes; an appropriate size so that no cleavage or fragmentation is required; or a product of environmental damage. The population of nucleic acids is used in combination with a target isolation probe for target enrichment.

Random cleavage can be achieved by enzymatic methods including: a single or a combination of nucleases such as Fragmentase® (New England Biolabs, Ipswich, Mass.), DNAse I, and Benzonase® (EMD, Gibbstown, N.J.), or other types of nucleases. Fragmentase is an endonuclease that generates dsDNA breaks in a time-dependent manner to yield 100 bp-800 bp DNA fragments. Benzonase® (EMD Millipore, Mass.) is genetically engineered endonuclease from *Serratia marcescens* that can effectively cleave both DNAs and RNAs. Other enzymatic methods include the use of Vvn nuclease alone or *Serratia* nuclease, or DNase I, or other nuclease in the art such as Shearase™ (Zymo Research, Irvine, Calif.) or Ion Shear™ (Life Technologies, Grand Island, N.Y.). Nicking enzymes can be used since the DNA is denatured after fragmentation.

Chemical means include use of magnesium or zinc ions to fragment RNA. Physical means can be used such as for example, sonication, nebulization, physical shearing, and heating. An example of a commercial mechanical shearing method is provided by Covaris (Woburn, Mass.).

Environmental nucleic acid damage may occur for example, during storage or through age or by application of fragmentation methods such as chemical-induced cleavage, enzyme-induced cleavage or cleavage by application of temperature or time. The term "damaged DNA" unless referred to otherwise is intended to mean any indels, any SNP, any modified base that is not associated with epigenetic regulation, any additional modifications to the target DNA. Various types of DNA damage are described in U.S. Pat. No. 7,700,283 and U.S. Pat. No. 8,158,388 incorporated by reference. An example of DNA damage is formalin-fixed paraffin-embedded (FFPE)-induced degraded DNA isolated from stored tissue or cells. The nucleic acids in the population may or may not be fragments of a larger nucleic acid.

Target sequences may occur in a population of nucleic acids. The term "target sequences" generally refers to a region of interest in a nucleic acid having special scientific, medical or agricultural relevance. "Target molecules" are independent chemical entities that hybridize to the probes etc. The terms are sometimes used interchangeably and their meaning will be made clear by the context in which the terms are used. Where the target nucleic acid is DNA, fragments of a large DNA such as a gDNA may partially or substantially form the population of nucleic acids from which target sequences are enriched. In this example, the target sequences of interest are only a subset of a nucleic acid sample hence the desirability of enrichment.

A target sequence may be an entire nucleic acid molecule or a portion of a nucleic acid molecule. Target sequences may include one or more of an exon sequence, a short stretch of a nucleic acid sequence around a mutation, one or more repeat sequence, a cDNA sequence, intron sequences and regulatory sequences. Examples of features of interest include single nucleotide polymorphisms (SNPs), gene fusions, copy number variations, and/or indels. When statistically meaningful, these features may be correlated with a phenotype of biological significance. Targets molecules may have sequences associated with one or more diseases, a phenotype of interest, regulation of metabolic pathways or other nucleic acids related or otherwise. A target molecule may include a continuous region of a DNA sequence or a collection of DNA sequences (e.g. cDNA sequences). The target molecule may be an RNA molecule such as an mRNA or an ncRNA. Examples of RNA target molecules include: ribosomal RNA (rRNAs), messenger RNAs (mRNAs), silencing RNAs (siRNAs), small nuclear RNAs (snRNA) microRNAs (miRNA) short interfering RNAs, (siRNAs) or long non-coding RNAs (lncRNAs).

Individual nucleic acids in a population of nucleic acids are generally the same size or larger than a target sequence contained within the population of nucleic acids. There is no upper limit on the size of a nucleic acid in the population or of a target sequence. However, the efficiency of handling large molecules and the capability of the sequencing platform to sequence the enriched target sequence may be size limiting. A target sequence in a large nucleic acid, for example a viral genome from a biopsy sample may be as large as 5000 nucleotides (nts) or 10,000 nts or larger. A length of a target sequence may be less than 500 nucleotides occurring in a genome or a large mRNA. For example, where a target sequence is in the 100 nts-200 nts range, the individual members of the population of nucleic acids might be around 500 nts. Intact gDNA or RNA can be fragmented to a suitable size for target enrichment. The target sequence length is one criteria to determine the fragment size. For example, the target sequence may be at least up to 100 bp-1000 bp, for example, 200 bp-800 bp for example, 300 bp-700 bp for example, 100 bp-300 bp or 100 bp-400 bp, or 100 bp-500 bp in length which favors the capture of complete target regions. Most exons are less than 200 bp. The methods described herein utilize modified nucleosides to achieve at least one of the following features: enhancement of hybridization specificity or duplex stability, increased nuclease resistance, introducing a site for enzyme cleavage, inhibiting enzyme ligation, inhibiting enzyme extension, or preventing polymerase amplification, among other features.

Examples of the use of modified nucleosides which are selected according to their intended purpose are described in Table 1. The term "nucleoside" as used herein includes the natural nucleosides, including 2'-deoxy and 2'-hydroxyl forms, e.g. as described in Kornberg, et al. *DNA Replication*, 2nd Ed. Freeman, San Francisco (1992). "Analogs" or "modified nucleoside" in reference to nucleosides includes synthetic nucleosides having modified base moieties and/or modified sugar moieties, e.g. described by Scheit, *Nucleotide Analogs*, John Wiley, New York (1980); Uhlman, et al. *Chemical Reviews*, 90:543-584 (1990), Crooke, et al. *Exp. Opin. Ther. Patents*, 6:855-870 (1996); Mesmaeker, et al. *Current Opinion in Structural Biology*, 5:343-355 (1995); and the like. Using probes or adaptors comprising several or many analogs with enhanced duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynyl pyrimidines, locked nucleic acids ("LNAs"), and like compounds. Such oligonucleotides are either available commercially or may be synthesized using methods described in the literature. Modified nucleosides (such as dUs or 8-Oxo-Gs) may be selected to permit cleavage of an oligonucleotide at the site of the analog by specific enzymes (uracil deglycosylase or fpg with endonuclease VIII) or to prevent amplification by a DNA polymerase (such as rNMPs). Modified nucleosides may be placed at the termini of probes or adaptors to permit or to block ligation. For example, where ligation is not desired, the 5' end of the probe or adaptor or both may be unphosphorylated or dephosphorylated and a 3' end may be capped with a dideoxynucleoside, an inverted nucleoside, or a carbon linker with or without an attached moiety. Modification of an oligonucleotide 5' end with a phosphate enables ligation. In addition, 3' modifications including but not limited to a dideoxynucleoside, an inverted nucleoside, or a carbon linker can be incorporated into probes or adaptors to prevent 3' extension by a polymerase. A 3' and/or 5' modification, on the adaptors, primers, target isolation probes or a second probes, such as one or more phosphothioates, may be utilized to protect against exonuclease digestion.

Specific examples of the use of modified nucleosides in aspects of this method include the use of a dideoxynucleoside to block ligation at a 3' end of an adaptor for example as illustrated in FIG. 1, 2A, 2B, 2C or 5C. A 3' modification to block ligation may be added to a target isolation probe in FIGS. 1 and 5C. A 3' modification on a second probe may block ligation as illustrated in FIGS. 4 and 5A-C. Addition of a dideoxy-modified nucleoside at the 3' end of the adaptor in FIG. 2C and the 3' end of a target isolation probe shown in FIG. 5A inhibits ligation, but permits subsequent extension of the 3' end with a DNA polymerase or reverse transcriptase with 3' exonuclease activity. In addition, the affinity domain and the capture domain are large entities attached to the 3' terminal nucleotide of the target isolation sequence (see FIGS. 3, 4, 5B and 5C). The affinity binding molecule at the 3' end may act as a separate blocking entity to prevent probe ligation and extension. In addition, the affinity binding molecule, bound to the capture domain, may sterically deter ligation of an adaptor to a partial target sequence as illustrated in FIGS. 3, 4, and 5B-C. In one aspect of the methods, a 3' probe does not require a 5' modification other than optionally 5' phosphorylation in the two probe method since it may be ligated to the adaptor prior to 5' exonuclease treatment and hence is protected from 5' exonuclease activity. In contrast it is desirable to prevent ligation on the 3' end of the probe in the single probe method so as to prevent conversion of the probes into an amplifiable library.

The boundaries of target sequences are preferably defined by one or more probes. The present methods utilize a target isolation probe and may additionally include a second probe which may be a single stranded molecule or a flap probe. The methods may additionally utilize small random sequence oligonucleotides and/or removable blocking oligonucleotides. The term "probe" as used herein refers to a single stranded polynucleotide with a known sequence that is complementary to a region of the target sequence identified for enrichment. The probe may be an oligonucleotide where an "oligonucleotide" refers to a synthetic nucleic acid of a length capable of being synthesized by a nucleic acid synthesizer. Alternatively, an oligonucleotide can be a naturally occurring, isolated and purified and optionally fragmented single stranded nucleic acid or partially single stranded and partially double stranded. The oligonucleotide can be DNA, RNA or both.

The size of a probe may be as long as or shorter than the target sequence. For example, a probe may comprise as many as 10,000 nts although more commonly the probe is less than 500 nts in length. Examples of probe length include 10-nts-200 nts, 25 nts-200 nts, 10 nts-150 nts, 10 nts-100 nts, 10-nts-75 nts, or 10 nts-50 nts. Probes may preferably have a length of 25 nts-200 nts. A pool of probes utilized in a single enrichment will preferably be the same or similar in size.

The term "target-isolation probe" as used herein, refers to a nucleic acid of defined length and sequence and which may be synthetic. The target isolation probe is associated with an affinity binding molecule and is capable of being immobilized via a capture domain on or in a solid or semi-solid substrate. The target-isolation probe defines at least one end of the target region in both one probe and two probe methods. In the one probe method described in FIGS. 1 and 2A-C, the target isolation probe defines both ends of the target sequence. The target isolation probe may be DNA, RNA or both and may additionally contain one or a plurality of modified nucleosides (see for example Table 1). A target isolation probe may lack a phosphate at the 5' end (see for example, FIGS. 1, 2A-C, and FIG. 5C) so as to inhibit ligation of a double stranded adaptor to the 5' end of the probe while permitting ligation between the 3' target sequence and the adaptor. The target isolation probe may include a 5' phosphate to facilitate ligation to a double stranded adaptor (see for example, FIGS. 3, 4, 5B). The 3' end of the target isolation probe may be modified to block ligation between the 3' probe end and a 5' end of an adaptor. The target isolation probe may also contain LNAs to increase the Tm and stabilize the hybridization of the probe to the target sequence.

The affinity domain associated with a 3' target isolation probe may be positioned at the 3' end or between the 3' end and the 5' end but preferably not at the 5' end of the 3' target isolation probe. The affinity domain associated with a 5' target isolation probe may be positioned at the 5' end or between the 3' end and the 5' end but preferably not at the 3' end of the 5' target isolation probe. If the target isolation probe defines the boundaries of the 3' and 5' end of the target sequence, the affinity domain is preferably positioned between the ends of the probe and not at the ends.

A second probe characterized by a sequence that is complementary to the 5' end of the target sequence may be used to define the 5' end of the target sequence if the target isolation probe hybridizes to the 3' end of the target sequence. Alternatively, the second probe may hybridize to the 3' end if the target isolation probe hybridizes to the 5' end.

In one example, a second probe is preferentially added after the target isolation probe is hybridized to the 3' end of target sequences followed by exonuclease digestion and removal of non-target nucleic acid adjacent to the sequence complementary to the target isolation probe. An advantage of hybridizing a second probe to the target sequence is that the possibility of false positives are reduced by the use of two target specific probes in the manner described. The target isolation probe and second probe may be alternatively added to the population of nucleic acids at the same time thereby defining the 3' end and the 5' end of the target region prior to exonuclease digestion of non-target nucleic acid sequences at one or both ends of the target sequence.

The term "flap probe" refers to a synthetic nucleic acid that contains a single-stranded portion that hybridizes to a target nucleic acid and a non-hybridizing double stranded region extending from the 3' end of the single stranded region. The target isolation probe may be a flap probe if it defines both ends of the target region in a one probe method as exemplified in FIG. 2B or it defines the 5' end of the target region in a two probe method as exemplified in FIG. 5B. The duplex 3' end of the flap probes may be formed by a hairpin structure or by a short, 3'-5' complementary oligonucleotide. A flap endonuclease, such as Fen-1, cleaves the 5' end of the target at a site opposite the 3' end of the single-stranded region of the flap probe and also removes 5' non-target sequences. Ligation of the nick results in addition of the 3' hairpin sequence or ligation of the strand complementary to the 3' region of the flap probe. The duplex 3' region may serve as an adaptor when ligated to the 5' end of the target sequence and may include the sequence elements routinely incorporated into an adaptor such as an NGS platform specific sequencing primer site, a library amplification primer site and/or a barcode and/or UID for sample identification.

In addition to the use of one or two probes as described above, removable blocking oligonucleotides may be used in the event that there might be repeat sequences in the population of nucleic acids. The term "removable blocking oligonucleotides", refers to a short nucleic acid sequences such as RNA which is amenable to RNAseH digestion or DNA with modified bases throughout its length where the blocking nucleic acid is capable of being digested while hybridized to target or non-target sequences. Where blocking RNA is used, this may be derived from cRNA copied from repetitive sequence enriched DNA (i.e., COT-1 DNA) or synthesized RNA encoding repetitive DNA sequences. In rare circumstance a repeat region is contained within a target nucleic acid sequence. More commonly, a repeat sequence or multiple repeat sequences occur throughout non-target DNA. The removable blocking oligonucleotides may be heated to allow denaturation and then cooled to permit hybridization to the population of nucleic acids. After hybridization with a target isolation probe and optionally a second probe, the removable blocking oligonucleotides are cleaved by RNaseHI or other suitable enzyme which may optionally combined with 5' and/or 3' exonucleases in a reaction mixture.

In addition to a target isolation probe and instead of a second probe, an oligonucleotide having a random sequence (NNNN etc.) of a length less than 10 nts for example 4 nts, 5 nts, 6 nts, 7 nts 8 nts or 9 nts may be hybridized to a single stranded region of the target sequence. This short oligonucleotide can be extended at the 3' end to form a blunt end or staggered end suitable for ligating an adaptor thereto.

Following hybridization of a target sequence within a population of nucleic acids to a complementary sequence in a target isolation probe, the duplex can be immobilized by means of a capture domain associated with a solid or semi-solid matrix. Once immobilized, any non-hybridized nucleic acids can be removed by washing with the result that the immobilized nucleic acids are enriched for target sequence.

The washing step required to remove non-target DNA may be less stringent that washing steps employed by commercially available hybridization enrichment methods, since these methods rely on the hybridization temperature, wash temperatures, and stringency of the wash buffers to exclude non-target molecules and enrich target molecules. As a result, these methods require a tight Tm range of the probes and carefully controlled wash conditions. The method presented here tolerates a much larger Tm range for the probes and less stringent washing, since the washing is only needed for the removal of completely unbound library fragments. The high specificity of the method is achieved by the use of exonuclease(s) in subsequent step(s), which will only create blunt ends, which can be ligated, if the correct target sequence is hybridized to the probe.

"Complementary" or "substantially complementary" refers to sequences of nucleic acid molecules that are capable of hybridization or base pairing to form a duplex between nucleotides or nucleic acids, such as, for instance, between the two strands of a double stranded DNA molecule or between an oligonucleotide probe or primer and a probe or primer binding site on a single stranded region of a nucleic acid. Complementary nucleotides are, generally, A and T (or A and U), or C and G. Two single stranded RNA or DNA molecules are said to be substantially complementary when the nucleotides of one strand, optimally aligned and compared and with appropriate, potential, recognized or phenotypically meaningful nucleotide insertions or deletions, pair with at least about 50% or at least 80% of the nucleotides of the other strand, or at least about 90% to 95%, and more preferably from about 98% to 100%. Alternatively, substantial complementarity exists when an RNA or DNA strand will hybridize under selective hybridization conditions to its complement to form a stable duplex. Typically, selective hybridization will occur when there is at least about 65% complementary over a stretch of at least 14 nts to 25 nts, preferably at least about 75%, more preferably at least about 90% complementary (see, Kanehisa, *Nucleic Acids Res.,* 12:203 (1984)). Specific hybridization can be achieved between a probe and a nucleic sample in which at least a portion of the nucleic acid sample and probe are single stranded and available for hybridization. A portion of the probe may be double stranded and thus not available for hybridization with a target sequence. A single strand region may be formed in a duplex or from a duplex by heat denaturation or other means well known in the art.

In an aspect of the method, hybridization of the target isolation probe is preferably conducted in solution. The conditions of hybridization can be relatively relaxed in the sense that mismatches within the hybridization sequence can be tolerated. For example, standard methods such as described by Tiquia, et al. *BioTechniques,* 6:664-675 (2004); or John, et al. *BioTechniques,* 44:259-264 (2008) can be used. Moreover fragments that have a predominance of AT/U base pairs, GC base pairs or a balanced mixture may all be effectively hybridized under the reaction conditions. Hybridization may range from 3 days to 30 minutes for example 1 hour-16 hours where the temperature may range significantly, and the hybridization mix may be varied. However, such hybridization period may be greater or less in other embodiments depending upon the hybridization conditions.

The hybridization product of a target isolation molecule hybridized to target nucleic acid is immobilized by binding of the affinity domain to a capture domain which may be coated on a solid or semi-solid support or may be the solid or semi-solid support itself as described below. The immobilization of nucleic acids in a population facilitates the subsequent steps of hybridization, exonuclease digestion, adaptor ligation and optionally amplification as well as permitting removal by washing of non-reactive materials, residual reagent and cleavage products thereby avoiding cross contamination and thus enhancing the ease and effectiveness of the target sequence enrichment.

The term "capture domain" as used herein, refers to a chemical structure or a moiety associated with a solid support (see below) or semi-solid support (such as agarose or acrylamide) for binding an affinity domain which in turn is associated with a target-isolation probe. The affinity domain may include a small molecule such as biotin, an antigen, a hapten, a modified nucleotide or a ligand where the small molecule is capable of binding or becoming cross-linked (e.g. photochemically or chemically further exemplified by aminethiol, crosslinking, maleimide crosslinking, N-hydroxysuccinimide or N-hydroxysulfosuccinimide, Zenon or SiteClick to the capture domain either directly or indirectly).

A variety of methods are known for attaching DNA to solid supports any of which may be used in aspects of the invention. These include covalent bonding to the support surface and non-covalent interaction (binding by adsorption, e.g. cationic surfaces) of the DNA with the surface. Typically, covalent immobilization involves the reaction of an active functional group on the DNA (affinity domain) with an activated functional group (capture domain) on the solid surface. Examples of reactive functional groups include amines, hydroxylamines, hydrazines, hydrazides, thiols, phosphines, isothiocyanates, isocyanates, N-hydroxysuccinimide (NHS) esters, carbodiimides, thioesters, haloacetyl derivatives, sulfonyl chlorides, nitro and dinitrophenyl esters, tosylates, mesylates, triflates, maleimides, disulfides, carboxyl groups, hydroxyl groups, carbonyldiimidazoles, epoxides, aldehydes, acyl-aldehydes, ketones, azides, alkynes, alkenes, nitrones, tetrazines, isonitriles, tetrazoles, and boronates. Examples of such reactions include the reaction between an amine and an activated carboxy group forming an amide, between a thiol and a maleimide forming a thioether bond, between an azide and an alkyne derivative undergoing a 1,3-dipolar cycloaddition reaction, between an amine and an epoxy group, between an amine and another amine functional group reacting with an added bifunctional linker reagent of the type of activated bis-dicarboxylic acid derivative giving rise to two amide bonds, or other combinations known in the art. Other reactions, such as UV-mediated cross-linking can be used for covalent attachment of DNA to solid supports.

The functional groups may be inherently present in the material used for the solid support or they may be provided by treating or coating the support with a suitable material. The functional group may also be introduced by reacting the solid support surface with an appropriate chemical agent.

Activation as used herein means a modification of a functional group on the solid support surface to enable coupling of a binding agent to the surface. Solid support as used herein is meant to comprise any solid (flexible or rigid) material onto which it is desired to capture and immobilize DNA.

Solid support may be biological, non-biological, organic, inorganic or a combination thereof, and may be in the form of particles, strands, precipitates, gels, sheets, tubings, spheres, containers, capillaries, pads, slices, films, plates, slides, and have any convenient shape, including flat, disc, sphere, circle, etc. The surface of the solid support may be composed of a variety of materials, for example, polymers, plastics, resins, polysaccharides, silica or silica-based materials, carbon, metals, inorganic glasses, membranes, etc., provided that the surface may support functional groups. Examples of a convenient solid support are e.g. glass surfaces such as glass slides, microtiter plates, and suitable sensor elements, in particular functionalized polymers (e.g. in the form of beads), chemically modified oxidic surfaces, e.g. silicon dioxide, tantalum pentoxide or titanium dioxide, or also chemically modified metal surfaces, e.g. noble metal surfaces such as gold or silver, copper or aluminium surfaces, magnetic surfaces, e.g. Fe, Mn, Ni, Co, and their oxides, quantum dots, e.g., III-V (GaN, GaP, GaAs, InP, or InAs) or II-VI (ZnO, ZnS, CdS, CdSe, or CdTe) semiconductors, or Ln-doped fluoride nanocrystals, rare earth-doped oxidic nanomaterials.

The "solid support" refers to a material or group of materials having a rigid or semi-rigid surface or surfaces. The solid support may be at least one surface of the solid support substantially flat, although in some embodiments it may be desirable to physically separate synthesis regions for different compounds with, for example, wells, raised regions, pins, etched trenches, or the like. Alternatively, the solid support may be beads, resins, gels, microspheres, or other geometric configurations. Examples of beads include, streptavidin beads, agarose beads, magnetic beads, Dynabeads® (Life Technologies, Grand Island, N.Y.), MACS® microbeads (Miltenyi Biotech, Auburn, Calif.), antibody conjugated beads (e.g., anti-immunoglobulin microbead), protein A conjugated beads, protein G conjugated beads, protein A/G conjugated beads, protein L conjugated beads, oligodT conjugated beads, silica beads, silica-like beads, anti-biotin microbead, anti-fluorochrome microbead, and BcMag™ (Bioclone, San Diego, Calif.) Carboxy-Terminated Magnetic Beads. Attaching the labeled nucleic acids to the support may comprise attaching biotin to the plurality of polynucleotides and coating one or more magnetic beads with streptavidin.

The solid support surface may be provided with a layer of a polymer. In such a case the polymers will carry the functional groups to be activated. The polymer may be selected from any suitable class of compounds, for example, polyethylene glycols, polyethylene imides, polysaccharides, polypeptides, or polynucleotides, just to mention a few. Attachment of the polymers to the support surface may be effected by a variety of methods which are readily apparent to a person skilled in the art. For example, polymers bearing trichlorosilyl or trisalkoxy groups may be reacted with hydroxyl groups on the substrate surface to form siloxane bonds. Attachment to a gold or silver surface may take place via thiol groups on the polymer. Alternatively, the polymer may be attached via an intermediate species, such as a self-assembled monolayer of alkanethiols. The type of polymers selected, and the method selected for attaching the polymers to the surface, will thus depend on the polymer having suitable reactivity for being attached to the substrate surface, and on the properties of the polymers regarding non-specific adsorption to, especially, DNA. The functional groups may be present on the polymer or may be added to the polymer by the addition of single or multiple functional groups. Optionally, a spacer arm can be used to provide flexibility to the binding DNA allowing it to interact with its environment in a way which minimizes steric hindrance with the solid support.

To immobilize a nucleic acid on the surface of a solid support, the activated functional groups on the surface may be present on the predefined regions only, or alternatively on the entire surface, and are reacted selectively with the functional groups present in the DNA molecules. The necessary reaction conditions, including time, temperature, pH, solvent(s), additives, etc. will depend on inter alia the particular species used and appropriate conditions for each particular situation will readily be apparent to the skilled person. Oligonucleotides can be synthesized to incorporate a desired functional group. Individual nucleotides can be modified either chemically or enzymatically with any type of functional group in order to provide the desired reactivity. This chemical or enzymatic functionalization can be extended to DNA molecules.

Functionalization of surfaces with biological materials can also be used for attaching DNA to solid supports. A solid support, e.g. a microplate, can be modified with a binder, e.g. an antibody (or antibody fragment) or another affinity binder, e.g. streptavidin. In that case the DNA molecule being modified with the corresponding affinity ligand, e.g. biotin, and another affinity binder, e.g. an antibody recognizing part of the sequence of a biomolecule. A binder as used herein means any agent that is a member of a specific binding pair, including, for instance polypeptides, such as proteins or fragments thereof; nucleic acids, e.g. oligonucleotides, polynucleotides, or a derivative thereof capable of undergoing base-pairing with its complementary strand. Examples of binders include agonists and antagonists for cell membranes, toxins and venoms, viral epitopes, antigenic determinants, hormones and hormone receptors, steroids, peptides, enzymes, substrates, cofactors, drugs, lectins, sugars, oligonucleotides, oligosaccharides, proteins, glycoproteins, cells, cellular membranes, organelles, cellular receptors, vitamins, viral epitopes, and immunoglobulins, e.g. monoclonal and polyclonal antibodies. Examples of binding pairs include biotin-streptavidin/avidin, hapten/antigen-antibody, carbohydrate-lectin, or others known to those skilled in the art.

Additional examples of specific binding pairs allowing covalent binding of DNA to a solid support are e.g. SNAP-Tag® (New England Biolabs, Ipswich, Mass.)/AGT and benzylguanine derivatives (U.S. Pat. Nos. 7,939,284; 8,367,361; 7,799,524; 7,888,090; and 8,163,479) or pyrimidine derivatives (U.S. Pat. No. 8,178,314), CLIP-Tag™ (New England Biolabs, Ipswich, Mass.)/ACT and benzylcytosine derivatives (U.S. Pat. No. 8,227,602), HaloTag® (Promega, Madison, Wis.) and chloroalkane derivatives (Los, et al. *Methods Mol. Biol.*, 356:195-208 (2007)), serine-beta-lactamases and beta-lactam derivatives (International Patent Application Publication No. WO2004/072232). In such as examples, DNAs can be functionalized with benzylguanine, pyrimidine, benzylcytosine, chloroalkane, or beta-lactam derivatives respectively, and subsequently be captured in a solid support modified with SNAP-tag/AGT, CLIP-tag/ACT, HaloTag or serine-beta-lactamases. Alternatively, DNA can be specifically or nonspecifically attached to SNAP-tag/AGT, CLIP-tag/ACT, HaloTag or serine-beta-lactamases and subsequently be captured in a solid support functionalized with benzylguanine, pyrimidine, benzylcytosine, chloroalkane, or beta-lactam derivatives, respectively. Further examples of specific binding pairs allowing covalent binding of DNA to a solid support are acyl carrier proteins and modifications thereof (binder proteins), which are coupled to a phosphopantheteine subunit from Coenzyme A (binder substrate) by a synthase protein (U.S. Pat. No. 7,666,612). Examples of proteins or fragments thereof allowing convenient binding of DNA to a solid support are e.g. chitin binding domain (CBD), maltose binding protein (MBP), glycoproteins, transglutaminases, dihydrofolate reductases, glutathione-S-transferase al (GST), FLAG tags, S-tags, His-tags, and others known to those skilled in the art. Typically, an oligonucleotide, DNA or fragment thereof is modified with a molecule which is one part of a specific binding pair and capable of specifically binding to a partner covalently or non-covalently attached to a solid support.

While the target DNA is immobilized as described above, one or more suitable 3' single stranded DNA exonuclease(s) such as 3' Exonuclease I and Exonuclease T may be added to remove non-target DNA to form a blunt end at a specified read start site of the target DNA. The "read start site" refers to a position at which sequencing of a nucleic acid molecule begins. The start site of the sequencing reads may be generated by digestion of single stranded nucleic acid using one or more nucleases to form a blunt end with a probe and then ligation of an adaptor such that the sequencing primer site immediate abuts the target nucleic acid sequence. As a result, the probe sequence selected defines the read start site. Preferably, the nuclease is a single-stranded 3' exonuclease that can form a blunt double stranded DNA (dsDNA) end, with no endonuclease activity. Accessory proteins such as single stranded binding proteins (SSB proteins) can be added. Klenow exo- and dATP may be added to provide a dA tail at the 3' end. The dA-tailing step is optional for use with a T-overhang 3' adaptor and is not required for a blunt end adaptor. For dA tailing, the enzyme used, its concentration, the incubation time, and temperature are not critical. However, the enzyme should add a single, untemplated nucleotide such as dA to the 3' end of dsDNA for a T-overhang adaptor.

A 5' exonuclease may be used to remove 5' non-target single stranded nucleic acid. If the 5' exonuclease requires heat denaturing temperatures to inactivate the nuclease, a rehybridization step may be added to rehybridize the probe to the template. If the 5' exonuclease leaves a 5' recessed end or a 5' overhang, a polymerase can be used digest a 3' overhang or fill in a 3' recessed end of the probe to form a blunt end or an end extended by one nucleotide. A polymerase with 3' exonuclease may be preferably used to form a blunt end, which can be ligated to a blunt 5' adaptor. Alternatively, a 3' exo-polymerase, such as Klenow (3'→5' exo-) or Bst can be substituted to form an end which can be ligated to a 5' adaptor with a T-overhang. Also, a dNTP mix of dATP, dCTP, dGTP and dUTP may be used in place of dATP, dCTP, dGTP, and dTTP. If the target is RNA, reverse transcriptase can be used with dNTPS or RNA polymerase with riboNTPs can be used. The fill-in polymerase, polymerase concentration, probe concentration, incubation times and temperatures can be varied as taught in the art (see for example, Tabor, et al. DNA dependent DNA polymerases in Ausebel, et al. *Current protocols in Molecular Biology,* 3.5.10-3.5.12 (1989), New York, John Wiley and Sons; Sambrook et al. (1989) Molecular Cloning, A laboratory Manual ($2^{nd}$ ed), p 5.44-5.47, CSH press).

After or during target enrichment, it may be desirable to ligate adaptor sequences to one or both ends of the target sequence. "Ligation" refers to the joining between the termini by covalent bond or linkage of two or more nucleic acids, e.g. oligonucleotides and/or polynucleotides. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley, et al. U.S. Pat. No. 4,883,750; Letsinger, et al. U.S. Pat. No. 5,476,930; Fung, et al. U.S. Pat. No. 5,593,826; Kool, U.S. Pat. No. 5,426,180; Landegren, et al. U.S. Pat. No. 5,871,921; Xu and Kool, *Nucleic Acids Research,* 27:875-881 (1999); Higgins, et al. *Methods in Enzymology,* 68:50-71 (1979); Engler et al. *The Enzymes,* 15:3-29 (1982); and Namsaraev, U.S. patent publication 2004/0110213.

Various types of adaptors that may be ligated to the ends of the target sequence are discussed below. The term "adaptor" refers to nucleic acids that are at least partially double stranded and contain sequences that are suitable as primer sites for amplification of the neighboring target sequence, sequencing primers that are specified by sequencing platforms and are located in a sequence adjacent to ligation site with the target sequence and unique identifiers for tracking nucleic acid source identity and/or barcodes for tracking sample identity. Examples of adaptors and their uses in sequencing reactions can be found in publications such as U.S. Pat. No. 5,888,737, U.S. Pat. No. 6,013,445, U.S. Pat. No. 6,060,245, U.S. Pat. No. 6,175,002, U.S. Pat. No. 7,741,463, U.S. Pat. No. 7,803,550, U.S. Pat. No. 8,029,993, U.S. Pat. No. 8,288,097, US 2004/0209299, US 2007/0172839 and US 2012/0238738.

A cleavable single strand hairpin adaptor, a double strand Y adaptor, a completely double stranded adaptor, or any other form of adaptor known in the art suitable for downstream sequencing on a commercial DNA sequencing platform may then be ligated to the 3' and/or 5' end of the target DNA. The cleavable site(s) within a hairpin adaptor may be dU(s), other modified nucleotide(s), one or more RNA nucleotides, or chemically cleavable site(s). These serve only as examples for a cleavable site that may include any of the modified bases described in US 2012/0238738. An advantage of using hairpin adaptors is that these adaptors are shorter than other adaptors in the art and can be efficiently used for ligation. Moreover, these adaptors are more resistant to residual single stranded exonuclease activity. In addition, ligation of the target molecule and the target isolation probe to a hairpin adaptor covalently links the target molecule to the affinity domain. After cleaving the hairpin adaptor and denaturing any double stranded regions, the single stranded region containing primer sites on the cleaved hairpin sequence can be used to amplify the target sequence.

The adaptor may include a T-overhang but could be blunt. The adaptor may contain a short adaptor sequence with additional sequence required for amplification on an NGS platform surface, or may supply the complete 3' or 5' sequence required by the NGS platform.

Adaptors at one or both ends optionally contain unique identifiers (UID) or molecular barcodes suitable for sequencing in a sequencing platform such as miSEQ HiSEQ® (Illumina, San Diego, Calif.), Ion Torrent® (Applied Biosystems (Carlsbad, Calif.), Nanopore based sequencer (Oxford Nanopore, Oxford, UK) or PacBio RS II (Pacific Biosciences, Menlo Park, Calif.). The term "unique identifier" (UID) as used herein refers to a tag or combination of tags associated with a polynucleotide whose identity (e.g., the tag DNA sequence) can be used to differentiate polynucleotides in a sample. In certain embodiments, the UID on a polynucleotide is used to identify the source from which the polynucleotide is derived. A source identifier may also be referred to as a barcode. For example, a nucleic acid sample may be a pool of polynucleotides derived from different sources, (e.g., polynucleotides derived from different individuals, different tissues or cells, or polynucleotides isolated at different times points), where the polynucleotides from each different source are tagged with a unique UID. As such, a UID provides a correlation between a polynucleotide and its source. In certain embodiments, UIDs are employed to uniquely tag each individual polynucleotide in a sample. Identification of the number of unique UIDs in a sample can provide a readout of how many individual polynucleotides are present in the sample or from how many original polynucleotides a manipulated polynucleotide sample was derived. Examples of identifiers utilized herein includes examples presented in Brenner, et al. *Proc. Natl. Acad. Sci.,* 97:1665-1670 (2000); Church, et al. *Science,* 240:184-188 (1988); Shoemaker, et al. *Nature Genetics,* 14:450-456 (1996); and Hardenbol, et al. *Nature Biotechnology,* 21: 673-678 (2003).

The adaptor concentration, ligase concentration, ligase reaction amounts, reaction buffer, reaction volume, incubation time and incubation temperature may be varied. In addition, a wash step after ligation makes possible the removal of unligated adaptors and adaptor dimers.

The term "primer" as used herein refers to an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually of a similar or same length selected from a size in the range of between 8 nts-100 nts in length, such as 10-nts-75 nts, 15 nts-60 nts, 15 nts-40 nts, 18 nts-30 nts, 20 nts-40 nts, 21 nts-50 nts, 22 nts-45 nts, 25 nts-40 nts, and so on, more typically in the range of between 18 nts-40 nts, 20 nts-35 nts, 21 nts-30 nts long, and any length between the stated ranges. Typical primers can be in the range of between 10-nts-50 nts long, such as 15 nts-45 nts, 18 nts-40 nts, 20 nts-30 nts, 21 nts-25 nts and so on, and any length between the stated ranges.

Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" has at least a 3' sequence complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The use of primers in embodiments of the method result in more uniform amplification of the target sequence compared to conventional PCR enrichment methods. In PCR enrichment, each primer pair is specific to a target sequence while single primer pair is used here for all target sequences in a population of nucleic acids Both single strand sense and antisense strands are preferably immobilized by a capture domain bound to a target isolation sequence hybridized in turn to the 3' end of the target region to form a double stranded DNA region suitable for ligation to an adaptor. At this time, any 3' single strand DNA region outside the 3' end of the target sequence has been preferably removed by exonuclease cleavage. After hybridizing a 5' probe at the 5' end of the target template and removing extraneous DNA outside the target region and addition of a 5' adaptor, the nucleic acid target template can be amplified and sequenced.

Where the 3' adaptor and the 5' adaptor are covalently attached to the target sequence, denaturation of the partially double stranded molecule results in a single stranded sequence with adaptor sequences at either end. These adaptor sequences now act as primer sites for DNA amplification by PCR or other amplification protocol known in the art which rely on two priming sequences. The enriched target DNA can be eluted from the capture domain using for example, heat, NaOH or formamide or alternatively may remain attached to beads if these are used for the capture domain. After amplification, the amplified library may be cleaned up using beads (see for example, Ampure® beads, Beckman Coulter (Brea, Calif.)) or by column purification (for example purification products from Qiagen, Valencia, Calif.) or other methods of DNA purification known in the art. The resulting library can then be quantified and sequenced.

Amplification methods optionally used herein after target enrichment may include any of polymerase chain reactions (PCRs), reverse transcriptase PCR(RT-PCR), rolling circle amplifications, real-time PCR" ligase chain reaction (LCR), transcription amplification, Q beta replicase mediated RNA amplification or isothermal amplification methods such as transcription mediated amplification, signal mediated amplification of RNA technology, strand displacement amplification, rolling circle amplification, loop-mediated isothermal amplification (LAMP), or helicase-dependent amplification (see for example, Gill et al. *Nucleosides Nucleotides Nucleic Acids*, 27:224-43 (2008); U.S. Pat. No. 5,242,794, U.S. Pat. No. 5,494,810, U.S. Pat. No. 4,988,617, and U.S. Pat. No. 6,582,938: U.S. Pat. No. 4,683,195; U.S. Pat. No. 4,965,188; U.S. Pat. No. 4,683,202; U.S. Pat. No. 4,800,159 (PCR); U.S. Pat. No. 5,210,015 (real-time PCR with TaqMan™ (Life Technologies, CA)); U.S. Pat. No. 6,174,670; Japanese patent publication JP 4-262799 (rolling circle amplification); Leone, et al. *Nucleic Acids Research*, 26: 2150-2155 (1998)).

Next generations sequencing (NGS) refers to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics, Hayward, Calif.); 454 pyrosequencing (454 Life Sciences/Roche Diagnostics, Branford, Conn.); solid-phase, reversible dye-terminator sequencing (Solexa/Illumina, San Diego, Calif.); SOLiD® technology (Applied Biosystems/ Life Technologies, Grand Isle, N.Y.); Ion semiconductor sequencing (Ion Torrene™, Life Technologies, Grand Isle, N.Y.); and DNA nanoball sequencing (Complete Genomics, Mountain View, Calif.). Descriptions of certain NGS platforms can be found in the following: Shendure, et al. *Nature*, 26:1135-1145 (2008); Mardis, *Trends in Genetics*, 24:133-141 (2007); Su, et al., *Expert Rev Mol Diagn*, 11(3):333-43 (2011); and Zhang et al. *J Genet Genomics*, 38(3):95-109 (2011).

An embodiment of the present methods described above may be summarized as follows: a target-enriched nucleic acid library may be generated by fragmenting to a predetermined size range, a nucleic acid sample, for example, gDNA from a eukaryotic organism or RNA transcripts into a population of nucleic acids, adding target isolation probes containing an affinity label for binding a matrix, where the target isolation probe spans the target sequence in a nucleic acid fragment, and using one or more 3' and 5' specific nuclease(s) or one or more 3' exonucleases and optionally one or more 5' exonucleases, such as ExoVII, simultaneously (e.g. in combination) or at different steps to remove non-target nucleic acid. A 3' adaptor and optionally a 5' adaptor may be added to the ends of the target DNA either simultaneously (e.g. in combination) or at different steps in the method. Amplification and sequencing of the enriched DNA may then follow. Barcodes and unique identifier sequences may optionally be included in the adaptor sequence or probe sequences.

In another aspect, 3' and 5' target probes where at least one probe is a target isolation probe comprising an affinity binding domain are hybridized either simultaneously (e.g. in combination) or at different steps, wherein the target length is defined by the hybridization of both probes and single-stranded non-target sequence is removed by exonucleases. Alternatively, a specific target isolation probe and a 3' exonuclease(s) may be used to define the 3' end of a target, followed by extension of a nonspecific probe, in the absence of 5' nucleases, in order to form an undefined 5' end of the target sequence.

Embodiments of the methods described herein are advantageous over previous hybridization based methods for reasons that include specifying start sites, so the target sequence is defined and there is no off target sequence, where in other hybridization methods the target sequence remain within a nucleic acid in the population with undefined boundaries with non-target sequence. In addition, both strands can be captured and tolerate more AT or GC-rich sequence within the targets than traditional hybridization methods.

Advantages of present embodiments over PCR based methods in the prior art is that artificial sequences are not introduced onto the ends of the targets. Moreover present embodiments are scaleable, have less amplification bias and allow the addition of unique UIDs to the target molecule. UIDs permit the identification of PCR duplicates of the same target molecule. As a result, PCR duplicates can be filtered during analysis, enabling accurate quantification of mutations or transcripts.

The term "kit" refers to any delivery system for delivering materials or reagents for carrying out a method of the invention. In the context of reaction assays, such delivery systems include systems that allow for the storage, transport, or delivery of reaction reagents (e.g., probes, enzymes, adaptors, primers etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes. A kit may be formulated for selecting and enriching target templates from a nucleic acid sample containing non-target and target sequences. The kit may include a 3' probe (a target isolation probe) comprising a first affinity binding domain either defined by the creator or manufacturer of the kit or by a researcher; a 5' probe; adaptors; primers: nucleases; ligase; polymerase(s); buffers; nucleotides; removable blocking oligonucleotides, and/or capture domains associated with a matrix. The kit may further comprise one or more buffer solutions and standard solutions for the creation of a DNA library.

All documents, cited herein are expressly incorporated by reference in their entirety for any purpose to the same extent as if each individual document was specifically and individually indicated to be incorporated by reference.

TABLE 1

Examples of the use of modified nucleotides in aspects of the methods are described in the application. The figures provide examples of where and how modifications may be used but the figures are not intended to be limiting for the purposes identified. Use of modifications to enable the uses described in the table are familiar in the art.

| | 5' Hairpin Adaptor | Target Isolation Probe | Flap Target Isolation Probe | Second Probe | Flap Second Probe |
|---|---|---|---|---|---|
| Amplification Primer Site | yes (all FIGS. except 2B, 5B) | no (all FIGS. except 2B) | yes (FIG. 2B) | no (FIG. 4, 5A, 5C) | yes (FIG. 5B) |
| Sequencing Primer Site | yes (all FIGS. except 2B, 5B) | no (all FIGS. except 2B) | yes (FIG. 2B) | no (FIG. 4, 5A, 5C) | yes (FIG. 5B) |
| Sample Idenifier | preferred (all FIGS. except 2B, 5B) | no (all FIGS. except 2B) | preferred (FIG. 2B) | no (FIG. 4, 5A, 5C) | preferred (FIG. 5B) |
| Molecule Identifier | optional (all FIGS. except 2B, 5B) | no (all FIGS. except 2B) | optional (FIG. 2B) | no (FIG. 4, 5A, 5C) | optional (FIG. 5B) |
| Modified Nucleotide to Cleave Strand | optional (all FIGS. except 2B, 5B - for each, must be used if no 5' mod to block ligation | no (all FIGS. except 2B) | yes - if probe is a hairpin (FIG. 2B) | no (FIG. 4, 5A, 5C) | yes - if probe is a hairpin (FIG. 5B) |
| Internal Modifications to Inhibit Amplification | no (all FIGS.) | optional (all FIGS.) | optional (FIG. 2B) | optional (FIG. 4, 5A, 5C) | optional (FIG. 5B) |
| Intenal Modifications to Increase Duplex Stability | optional (all FIGS. except 2B, 5B) | optional (all FIGS.) | optional (FIG. 2B) | optional (FIG. 4, 5A, 5C) | optional (FIG. 5B) |
| 3' Modifications to Inhibit Ligation | no (all FIGS. except 2B, 5B) | preferred (FIGS. 3, 4, 5B, 5C) optional (FIG. 1, 2A, 2C) | optional (FIG. 2B) | no (FIG. 4, 5A, 5C) | optional (FIG. 5B) |
| 3' Modifications to Inhibit Extension | n/a (all FIGS.- except 2B, 5B) | yes (FIGS. 3, 4) optional (FIG. 1, 2A-C, 5B-C) no (FIG. 5A) | optional (FIG. 2B) | no (FIG. 4, 5A, 5C) | optional (FIG. 5B) |
| 3' Modifications to Inhibit Digestion | optional (all FIGS. except 2B, 5B) | optional (all FIGS. except 2B) | optional (FIG. 2B) | optional (FIG. 4, 5A, 5C) | optional (FIG. 5B) |
| 5' Modifications to Inhibit Ligation | optional (all FIGS. except 2B, 5B - for each, must be used if no cleavable nucleotide. | optional (FIG. 1, 2A, 2C, 5C) no (FIG. 3, 4, 5A, 5B) | optional (FIG. 2B) | optional (FIG. 4, 5A, 5C) | optional (FIG. 5B) |
| 5' Modifications to Inhibit Digestion | optional (all FIGS. except 2B, 5B) | optional (all FIGS. except 2B, 5B) | optional (FIG. 2B) | optional (FIG. 4, 5A, 5C) | optional (FIG. 5B) |
| 3' Modifications to Deter Ligation of Hybridized Strand | no (all FIGS. except 2B, 5B) | preferred (FIG. 2C, 3, 4, 5B, 5C) no (FIG. 1, 2A, 5A) | no (FIG. 2B) | no (FIG. 4, 5A, 5C) | no (FIG. 5B) |

TABLE 1-continued

Examples of the use of modified nucleotides in aspects of the methods are described in the application. The figures provide examples of where and how modifications may be used but the figures are not intended to be limiting for the purposes identified. Use of modifications to enable the uses described in the table are familiar in the art.

| | 5' Hairpin Adaptor | Target Isolation Probe | Flap Target Isolation Probe | Second Probe | Flap Second Probe |
|---|---|---|---|---|---|
| 5' Modifications to Deter Ligation of Hybridized Strand | no (all FIGS. except 2B, 5B) | no (all FIGS. except 2B) | no (FIG. 2B) | no (FIG. 4, 5A, 5C) | no (FIG. 5B) |
| Affinity Domain | no (all FIGS. except 2B, 5B) | yes (all FIGS. except 2B) | yes (FIG. 2B) | no (FIG. 4, 5A, 5C) | no (FIG. 5B) |
| Amplification Primer Site | yes (all FIGS. except 2B, 5B) | no (all FIGS. except 2B) | yes (FIG. 2B) | no (FIG. 4, 5A, 5C) | yes (FIG. 5B) |
| Sequencing Primer Site | yes (all FIGS. except 2B, 5B) | no (all FIGS. except 2B) | yes (FIG. 2B) | no (FIG. 4, 5A, 5C) | yes (FIG. 5B) |
| Sample Identifier | preferred (all FIGS. except 2B, 5B) | no (all FIGS. except 2B) | preferred (FIG. 2B) | no (FIG. 4, 5A, 5C) | preferred (FIG. 5B) |
| Molecule Identifier | optional (all FIGS. except 2B, 5B) | no (all FIGS. except 2B) | optional (FIG. 2B) | no (FIG. 4, 5A, 5C) | optional (FIG. 5B) |
| Modified Nucleotide to Cleave Strand | optional (all FIGS. except 2B, 5B - for each, must be used if no 5' mod to block ligation | no (all FIGS. except 2B) | yes - if probe is a hairpin (FIG. 2B) | no (FIG. 4, 5A, 5C) | yes - if probe is a hairpin (FIG. 5B) |
| Internal Modifications to Inhibit Amplification | no (all FIGS.) | optional (all FIGS.) | optional (FIG. 2B) | optional (FIG. 4, 5A, 5C) | optional (FIG. 5B) |
| Internal Modifications to Increase Duplex Stability | optional (all FIGS. except 2B, 5B) | optional (all FIGS.) | optional (FIG. 2B) | optional (FIG. 4, 5A, 5C) | optional (FIG. 5B) |
| 3' Modifications to Inhibit Ligation | no (all FIGS. except 2B, 5B) | preferred (FIGS. 3, 4, 5B, 5C) optional (FIG. 1, 2A, 2C) | optional (FIG. 2B) | no (FIG. 4, 5A, 5C) | optional (FIG. 5B) |
| 3' Modifications to Inhibit Extension | n/a (all FIGS.- except 2B, 5B) | yes (FIGS. 3, 4) optional (FIG. 1, 2A-C, 5B-C) no (FIG. 5A) | optional (FIG. 2B) | no (FIG. 4, 5A, 5C) | optional (FIG. 5B) |
| 3' Modifications to Inhibit Digestion | optional (all FIGS. except 2B, 5B) | optional (all FIGS. except 2B) | optional (FIG. 2B) | optional (FIG. 4, 5A, 5C) | optional (FIG. 5B) |
| 5' Modifications to Inhibit Ligation | optional (all FIGS. except 2B, 5B - for each, must be used if no cleavable nucleotide. | optional (FIG. 1, 2A, 2C, 5C) no (FIG. 3, 4, 5A, 5B) | optional (FIG. 2B) | optional (FIG. 4, 5A, 5C) | optional (FIG. 5B) |
| 5' Modifications to Inhibit Digestion | optional (all FIGS. except 2B, 5B) | optional (all FIGS. except 2B, 5B) | optional (FIG. 2B) | optional (FIG. 4, 5A, 5C) | optional (FIG. 5B) |
| 3' Modifications to Deter Ligation of Hybridized Strand | no (all FIGS. except 2B, 5B) | preferred (FIG. 2C, 3, 4, 5B, 5C) no (FIG. 1, 2A, 5A) | no (FIG. 2B) | no (FIG. 4, 5A, 5C) | no (FIG. 5B) |

TABLE 1-continued

Examples of the use of modified nucleotides in aspects of the methods are described in the application. The figures provide examples of where and how modifications may be used but the figures are not intended to be limiting for the purposes identified. Use of modifications to enable the uses described in the table are familiar in the art.

| | 5' Hairpin Adaptor | Target Isolation Probe | Flap Target Isolation Probe | Second Probe | Flap Second Probe |
|---|---|---|---|---|---|
| 5' Modifications to Deter Ligation of Hybridized Strand | no (all FIGS. except 2B, 5B) | no (all FIGS. except 2B) | no (FIG. 2B) | no (FIG. 4, 5A, 5C) | no (FIG. 5B) |
| Affinity Domain | no (all FIGS. except 2B, 5B) | yes (all FIGS. except 2B) | yes (FIG. 2B) | no (FIG. 4, 5A, 5C) | no (FIG. 5B) |

EXAMPLES

The examples below describe specific temperatures, incubation times and buffers. However, the conditions are not intended to be limiting. A person of ordinary skill in the art would know that the human gDNA exemplified here as a starting material for enriching various sequences therefrom is not intended to be limiting nor should the extent to which pH, buffer and salt conditions and incubation times could be varied to effect a similar degree of hybridization or amplification be limited to the conditions specified below. Similarly, the description of biotin as an affinity domain is not intended to be limiting. Specific adaptors with specific cleavable sites are also described below by way of an example and is not intended to be limiting. An order of steps is described as an example. It will be understood that order of steps may be modified. Moreover, certain steps may be added or deleted as expedient.

Example 1

Figure 1:
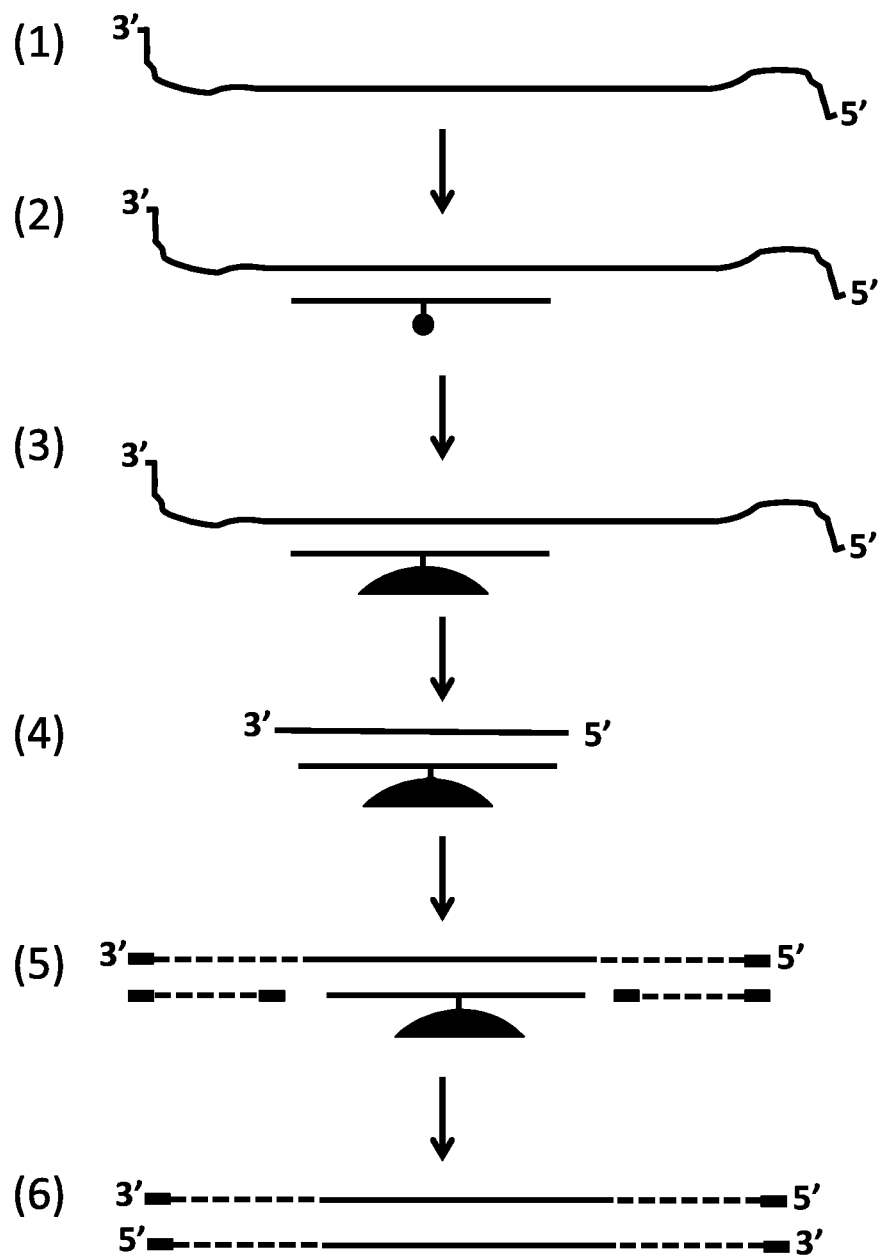
FIG. 1 shows a schematic of a method for target selection and enrichment. (1) depicts a single stranded nucleic acid or one strand of a heat denatured double stranded nucleic acid. (2) depicts a target isolation probe covalently linked to an affinity domain (♦), at a position between but not at the 3' and 5' ends of the target isolation probe, hybridized to (1). Here, the target isolation probe is hybridized to the entire length of the target nucleic acid sequence. The target isolation probe can include modifications on either or both the 3' and 5' ends to prevent exonuclease degradation, ligation, and/or polymerase extension. Modifications may include one or more of the following: inverted bases; carbon linkers; phosphorothioate linkages; and dideoxynucleotides. In addition, internal modifications may be included to prevent amplification of the target isolation probes, such as one more dUs or one or more ribonucleotides. (3) depicts the binding of (2) to a capture domain (▬). Nucleic acid that is not bound to the capture domain is removed by washing. (4) corresponds to the product of digestion by one or more 3' and 5' single strand DNA exonucleases or RNA exonucleases resulting in double-stranded blunt ends on both the 3' and 5' ends of the target molecule/target isolation probe duplex. The 3' and 5' digestion can be performed together or in succession. After digestion, the enzyme(s) and buffer are washed away. (5) depicts the target nucleic acid to which adaptors have been ligated to each end of the target sequence. Ligation to the target isolation probe is blocked. The adaptors used here could be: NGS platform-specific adaptors ligated to the ends using a DNA ligase such as T4 DNA ligase for DNA targets or a RNA ligase such as T4 RNA Ligase 2 for RNA targets; adaptors which contain a single nucleotide overhang (ligated to the 3' ends extended by a single nucleotide, such as the addition of dA with Klenow (exo-) on to DNA targets); Y structure or hairpin adaptors with a cleavable site so that unique sequences can be specifically added to the 3' and 5' ends of the target DNA or RNA; fully complementary double-stranded DNA (dsDNA) adaptors, or dsDNA adaptors with an single-stranded DNA (ssDNA) overhang at the opposite end from the ligation junction. These adaptors can contain one or more modifications such as dideoxynucleotides, inverted nucleotides, or the absence of 5' phosphates on the adaptor terminus that is not intended for ligation to target nucleic acid so as to avoid ligation to the target isolation probe and/or concatamerization. The adaptor strand that does ligate to the 3' end of the target DNA can contain a 5'-phosphate for ligation. Alternatively, this adaptor strand can lack a 5'-phosphate if the 3' end of the probe and the 5' end of its adaptor are not modified to inhibit ligation. In this case, the adaptor sequence can be added to the 3' end of the target by nick translation after ligation of the probe to the adaptor. Unligated adaptor, enzymes, and buffer are then washed away. One or both adaptors may contain a unique DNA sequence (UID) to identify the nucleic acid sample from which the target sequence came or a barcode to identify the individual organism from which the nucleic acid sample or samples were derived. Use of UIDs and/or barcodes facilitates sample validation and identification in multiplexing reactions (6) corresponds to the product of the optional PCR amplification of adaptor-ligated target molecules after elution from the solid support. If PCR or RT-PCR is used, the PCR primers may add additional sequence, such as sequence required by the sequencing platform, or may only contain sequence complementary to the adaptors. Alternatively, if the adaptor-ligated target molecules are immobilized via the affinity domain that in turn are associated with the capture domain, the immobilized target molecules may be added directly to an amplification reaction without the need for elution from the solid or semi-solid matrix into solution. The resulting library can then be quantified and sequenced.

A Method for Enriching for Target Sequence for Sequencing with One Target Isolation Probes Human gDNA (1 µg) was sheared with a Covaris device following the manufacturer's protocol for 300 bp fragments (FIG. 1 (1)). The sheared DNA was added to 25 µl hybridization reaction buffer containing 20 nmol of target isolation probe which was 100 bases in length and associated with biotin where the 100 base sequence was complementary to the 100 nt target sequence (FIG. 1 (2)). The hybridization reaction was performed according to John, et al. *BioTechniques*, 44, 259-264 (2008). After hybridization, the target isolation probe/target DNA duplexes were bound to 50 µl of hydrophilic streptavidin beads (New England Biolabs, Ipswich, Mass.) for 30 minutes (FIG. 1 (3)) and washed with standard BW Buffer (5 mM Tris-HCl (pH 7.5), 0.5 mM EDTA, 1M NaCl).

As utilized throughout, a "reaction mixture" means a solution containing all the necessary reactants for performing a reaction, which may include, but not be limited to, buffering agents to maintain pH at a selected level during a reaction, enzymes, substrates, salts, co-factors, scavengers, and the like.

The beads were resuspended in a 50 µl reaction mix containing 1× NEBuffer 4, 2.5 U Exonuclease T (New England Biolabs, Ipswich, Mass.) and 2.5 U Exonuclease 1 (New England Biolabs, Ipswich, Mass.) and incubated for 10 minutes at 37° C. The magnetic beads were washed and resuspended in 50 µl of 1× NEBuffer 2 containing 30 units of RecJf (New England Biolabs, Ipswich, Mass.) and incubated for 10 minutes at 20° C. (FIG. 1 (4)).

The magnetic beads were washed and resuspended in 50 µl of dA-Tailing reaction mix (New England Biolabs, Ipswich, Mass.) and incubated for 30 minutes at 37° C. The beads were then washed and resuspended in 45 µl of 1× Quick Ligation buffer (New England Biolabs, Ipswich, Mass.) and the NEBNext® adaptor for Illumina (New England Biolabs, Ipswich, Mass.). 5 µl of Quick T4 DNA ligase (New England Biolabs, Ipswich, Mass.) was added to the ligation mixture and incubated at room temperature for 15 minutes (FIG. 1 (5)).

The magnetic beads were then washed and resuspended in a 1× HotStart OneTaq® PCR Master Mix (New England Biolabs, Ipswich, Mass.) containing 5 µl of USER™ enzyme (New England Biolabs, Ipswich, Mass.) and NEBNext® primers for Illumina (New England Biolabs, Ipswich, Mass.). The PCR mixture was incubated at 37° C. for 15 minutes and following PCR cycling conditions is used: 95° C. for 2 minutes followed by 25 cycles of 95° C. for 30 seconds, 60° C. for 30 seconds and 72° C. for 1 minute (FIG. 1 (6)). At the end of the 25 cycles, the PCR mixture incubated at 72° C. for 5 minutes. The PCR products obtained from the target sequences were then sequenced using conventional methods.

Example 2

A Variation on the Method for Enriching for Target Sequence for Sequencing with One Target Isolation Probes The protocol in Example 1 and FIG. 1 was followed through binding to streptavidin beads (1)-(3) followed by steps shown in FIG. 2A (7)-(11).

The beads were resuspended in a 50 µl reaction mix containing 1× NEBuffer 4, 2.5 U Exonuclease T and 2.5 U Exonuclease I and incubated for 10 minutes at 37° C. (7).

The magnetic beads were washed and resuspended in 50 µl of dA-Tailing reaction mix and incubated for 30 minutes at 37° C. The beads were then washed and resuspended in 45 µl of 1× Quick Ligation and the NEBNext adaptor for Illumina. 5 µl of Quick T4 DNA ligase was added to the ligation mixture and incubated at room temperature for 15 minutes FIG. 2A (8).

The magnetic beads were washed and resuspended in 50 µl of 1× Exonuclease VII buffer containing 20 units of Exonuclease VII (Epicentre, Madison, Wis.) and incubated for 10 minutes at 30° C. (9). The enzyme was heat-inactivated following the manufacturer's protocol. The beads were washed and resuspended in 50 µl 1× NEBuffer 2 containing 15 U T4 DNA polymerase (New England Biolabs, Ipswich, Mass.) and 100 µM dNTPs. The reaction was incubated for 30 minutes at 20° C.

The beads were then washed and resuspended in 45 µl of 1× Quick Ligation buffer and the NEBNext adaptor for Illumina. 5 µl of Quick T4 DNA ligase was added to the ligation mixture and incubated at room temperature for 15 minutes (10).

USER cleavage of the adaptors and PCR amplification were performed as described in Example 1.

Example 3

A Method for Enriching for Target Sequence for Sequencing with One Flap Probe

The protocol described in Example 1 was followed through ligation of the 3' adaptor using a flap target isolation probe (see FIG. 2B). The flap target isolation probe is characterized by a single-stranded 3' region specific to the 5' end of the target sequence, an internal biotin-dT, a 5' hairpin containing a cleavable dU, a NGS platform-specific sequencing primer site, a library amplification primer site and a unique sample identifier sequence (1-3, 12-13). After ligation of the 3' adaptor, the beads were washed and resuspended in 50 µl of 1×REC Reaction Buffer 12 (Trevigen, Gaithersburg, Md.) containing 5 µl of 10×BSA additive (Trevigen, Gaithersburg, Md.) and 0.5 U Human Fen-1 (Trevigen, Gaithersburg, Md.) and incubated for 30 minutes at 30° C. (14). The beads were then washed and resuspended in 45 µl of 1× Quick Ligation buffer and 5 µl of Quick T4 DNA ligase and incubated at room temperature for 15 minutes.

USER cleavage of the adaptors and PCR amplification were performed as described in Example 1 (15).

Example 4

A Variation on the Method for Enriching for Target Sequence for Sequencing with One Target Isolation Probes The protocol in Example 1 was followed through single stranded 3' and 5' digestion (FIG. 1 (1)-(4) and FIG. 2C (16)-(18)) using a target isolation probe with a 3'-dideoxynucleotide. The beads were washed and resuspended in 45 µl of 1× Quick Ligation buffer and 10 µl of 50 µM 3' blunt-ended hairpin DNA adaptor and 5 µl of Quick T4 DNA ligase was added to the ligation mixture and incubated at room temperature for 15 minutes (16). The 3' adaptor sequence contained an NGS platform-specific sequencing primer site, a 5' phosphate and a 3'-dideoxynucleotide.

After the beads were washed, the target/probe duplex was blunt ended, dA-tailed and the 5' adaptor was ligated to the target, and the targets were amplified using the NEBNext Ultra DNA Library Prep Kit for Illumina (New England Biolabs, Ipswich, Mass.), following the manufacturers protocol for library preparation without size selection (17), (18).

Example 5

Figure 3:
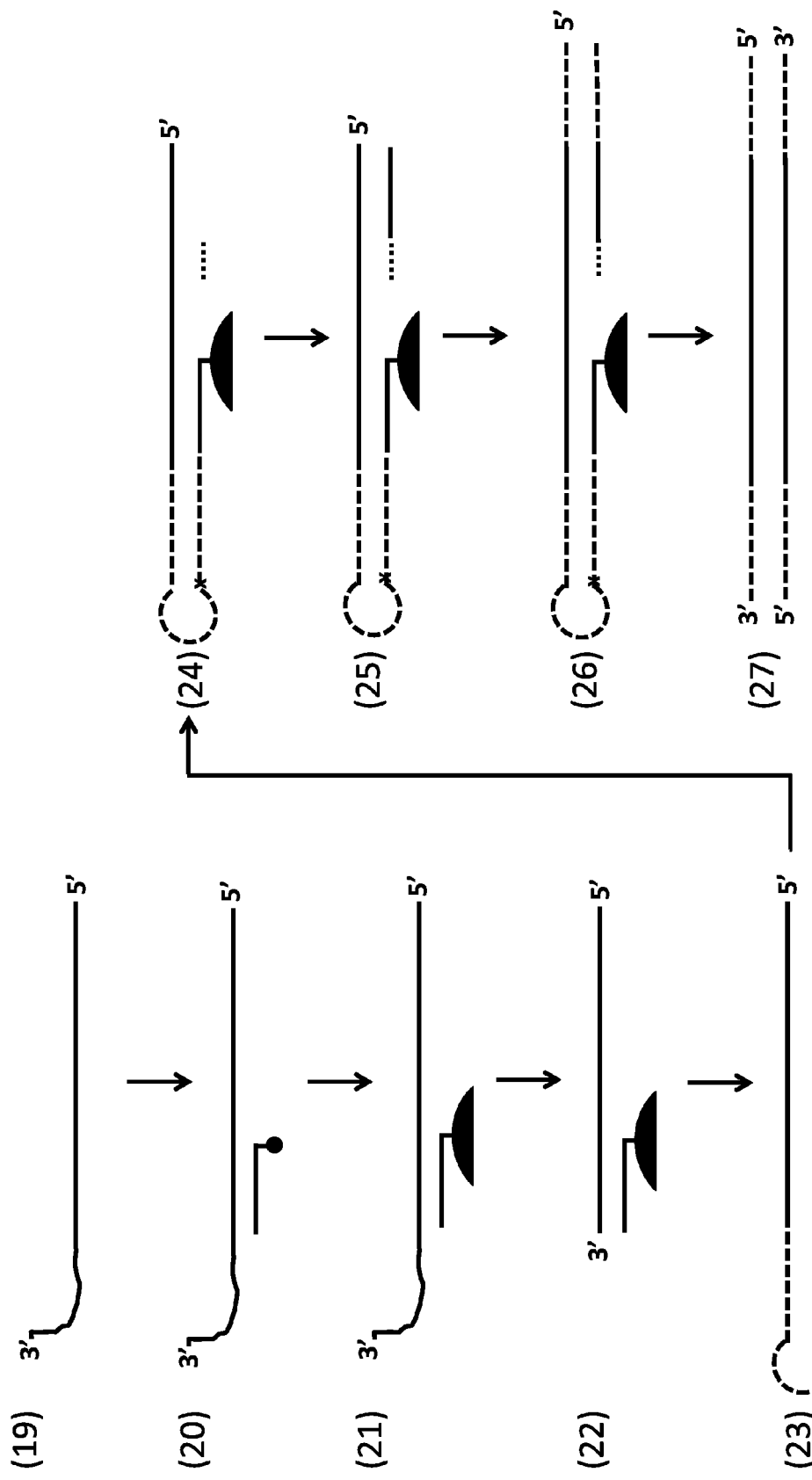
FIG. 3 shows a two probe method for target selection and enrichment which utilizes as one probe, the target isolation probe and as a second probe a small variable (random) oligonucleotide. (19) depicts a single stranded nucleic acid that may be one strand of a heat denatured fragment resulting from mechanical or enzymatic fragmentation of a larger nucleic acid. (20) is a 3' target isolation sequence hybridized to the 3' end of the target sequence and covalently linked to an affinity domain where the affinity domain is located at a position not at the 5' end of the target isolation probe. The target isolation probe can include modifications on the 3' end to prevent exonuclease degradation, ligation, and/or polymerase extension. Examples of modifications include inverted bases, carbon linkers, phosphorothioate linkages and dideoxynucleotides. The target isolation probe can include modifications on the 5' end to prevent exonuclease degradation, such as phosphorothioate linkages. In addition, internal modifications may be included to prevent amplification of the probes, such as one more dUs or one or more ribonucleotides. (21) depicts immobilization of (20) to a capture domain. Nucleic acid that is not bound to the capture domain is removed by washing. (22) is the product of digestion by 3' single strand DNA exonuclease(s) or RNA exonuclease(s) leaving a double-stranded blunt end on the 3' end of the target nucleic acid/target isolation probe duplex. After digestion, the enzyme(s) and buffer are washed away. (23) depicts a hairpin adaptor having a cleavable site (X) covalently linked to the 3' target sequence and the 5' end of the target isolation probe. (24) depicts a random oligonucleotide hybridized to the 5' region of the target nucleic acid of (23). (25) is the product of extension of the 3' end of the random primer by a DNA polymerase, RNA polymerase or reverse transcriptase to form a blunt end. Standard deoxynucleotides or ribonucleotides can be used for the extension or, a mixture containing one or more modified dNTPs, such as dUTP, can be used to later digest any extended sequence. After blunting, the enzyme(s) and buffer are washed away. (26) is (25) to which a 5' adaptor is attached (as described for example in FIG. 1). (27) is the amplification product of (26).

A Method for Enriching for Target Sequence for Sequencing Using a Target Isolation Probe and a Random Oligonucleotide Human gDNA (1 µg) was sheared with a Covaris device following the manufacturer's protocol for 500 bp fragments (FIG. 3 (19)). The sheared DNA was added to a 25 µl hybridization reaction mixture containing 20 nmol of 3' target isolation probes, 50 bases in length, specifically complementary to the 3' end of a 100 bp-300 bp nucleotide target sequence within the 500 bp gDNA fragment (FIG. 3 (20)) using the technique described by Tiquia, et al. (2004)). After hybridization, the 3' target isolation probe/target DNA duplexes were bound to 50 µl of hydrophilic streptavidin beads for 30 minutes following the manufacturer's protocol (FIG. 3 (21)).

The beads were resuspended in a 50 µl reaction mix containing 1× NEBuffer 4, 2.5 U Exonuclease T and 2.5 µl Exonuclease 1 and incubated for 10 minutes at 37° C. (FIG. 3 (22)). The magnetic beads were washed and resuspended in 50 µl of dA-Tailing reaction mix and incubated for 30 minutes at 37° C. The beads were then washed and resuspended in 45 µl of 1× Quick Ligation buffer and a 10 µl of 50 µM hairpin adaptor with a 3' T overhang containing a cleavable nucleic acid base of dU and 5 µl of Quick T4 DNA ligase was added to the ligation mixture and incubated at room temperature for 15 minutes (FIG. 3 (23)). The 3' adaptor sequence contained an NGS platform-specific sequencing primer site, a library amplification primer site and a unique strand identifier sequence, and a 3' dT-overhang.

After ligation, the beads were washed and resuspended in 50 µl 1× NEBuffer 2 containing an additional 20 nmol of random hexamer. The reaction was heated for 5 minutes at 95° C., then transferred to ice (FIG. 3 (24)) before addition of 15 units Klenow (exo-) DNA polymerase (New England Biolabs, Ipswich, Mass.) and 100 µM dNTPs. The reaction was incubated for 10 minutes at 20° C. followed by 20 minutes at 37° C. (FIG. 3 (25)).

The beads were then washed and resuspended in 45 µl of 1× Quick Ligation buffer (New England Biolabs, Ipswich, Mass.) and a 5' single-strand hairpin adaptor containing a cleavable nucleic acid base of dU and 5 µl of Quick T4 DNA ligase (New England Biolabs, Ipswich, Mass.) was added to the ligation mixture and incubated at room temperature for 15 minutes (FIG. 3 (26)). The 5' adaptor sequence contained an NGS platform-specific sequencing primer site, a library amplification site and a barcode sequence for sample identification.

The magnetic beads were then washed and resuspended in a 1× HotStart OneTaq PCR Master Mix containing 5 µl of USER enzyme and 2.5 µl each of 10 µM amplification primers complementary to the 3' and 5' library amplification sites. The PCR mixture was incubated at 37° C. for 15 minutes and following PCR cycling conditions is used: 95° C. for 2 minutes followed by 25 cycles of 95° C. for 30 seconds, 60° C. for 30 seconds and 72° C. for 1 minute (FIG. 3 (27)). At the end of the 25 cycles, the PCR mixture incubated at 72° C. for 5 minutes. The PCR products obtained from the target sequences were then sequenced using conventional methods.

Example 6

A Variation on the Method for Enriching for Target Sequence for Sequencing Using Target Isolation Probe and a Second Probe The protocol described in Example 5 was followed through ligation of the 3' adaptor ((19)-(23)). After ligation, the magnetic beads were washed and resuspended in 50 µl of 1× Exonuclease VII buffer with 20 nmol of 5' target isolation probes, 50 bases in length, complementary to the 5' end of the target sequences. The target isolation probes were annealed to the targets by heating for 5 minutes at 95° C., followed by slowly cooling to 30° C. (FIG. 4 (28)). 10 U of Exonuclease VII was added to the reaction and incubated for an additional 10 minutes at 37° C. (FIG. 4 (29)). The enzyme was heat-inactivated following the manufacturer's protocol. The beads were washed and resuspended in 50 µl 1× NEBuffer 2 (New England Biolabs, Ipswich, Mass.) containing an additional 20 nmol of 5' target isolation probe. The reaction was heated for 5 minutes at 95° C., followed by slowly cooling to 30° C. before addition of 15 U T4 DNA polymerase (New England Biolabs, Ipswich, Mass.) and 100 µM dNTPs. The reaction was incubated for 30 minutes at 20° C.

After the beads were washed, ligation of the 5' adaptor, USER cleavage of the adaptors and PCR amplification were performed as described in Example 4 using a hairpin adaptor with a 3'-T overhang ((FIG. 4 (30), (31)).

Example 7

A Variation on the Method for Enriching for Target Sequence for Sequencing with Two Probes The protocol described in Example 4 was followed through 5' exonuclease digestion and heat inactivation ((19)-(23), (28)-(29)) using 3' target isolation probes with an internal, rather than a 3' biotin. After heat inactivation, the beads were washed and resuspended in 50 µl 1× NEBuffer 2 containing 15 units Klenow (exo-) DNA polymerase and 100 µM dNTPs. The reaction was incubated for 10 minutes at 20° C. followed by 20 minutes at 37° C. (32).

After the beads were washed, ligation of the 5' adaptor, USER cleavage of the adaptors and PCR amplification were performed as described in Example 5 ((26), (27)).

Example 8

A Method for Enriching for Target Sequence for Sequencing with a Target Isolation Probe and a 5' Flap Probe The protocol described in Example 6 was followed through ligation of the 3' hairpin adaptor (FIG. 3, (19)-(23)). After ligation of the 3' adaptor, the beads were washed and resuspended in 50 µl of 1×REC Reaction Buffer 12 containing 20 nmol of flap 5' probe. The flap probe consisted of a single-stranded 3'-region complementary to the 5' end of the target and a 5' hairpin containing a cleavable dU, an NGS platform-specific sequencing primer site, a library amplification primer site and a unique sample identifier sequence. The probe was annealed to the 5' end of the target sequence by heating for 5 minutes at 95° C., followed by slowly cooling to 30° C. (35).

After annealing 5 µl of 10×BSA additive and 0.5 units Human Fen-1 was added to remove the 5' single stranded region and the reaction was incubated for 30 minutes at 30° C. (36). The beads were then washed and resuspended in 45 µl of 1× Quick Ligation buffer and 5 µl of Quick T4 DNA ligase for repairing the nick between the second strand of the flap probe and the target DNA and incubated at room temperature for 15 minutes.

The magnetic beads were then washed and resuspended in a 1× HotStart OneTaq PCR Master Mix containing 5 µl of USER enzyme and amplification primers. The PCR mixture was incubated at 37° C. for 15 minutes and the following PCR cycling conditions were used: 95° C. for 2 minutes followed by 25 cycles of 95° C. for 30 seconds, 60° C. for 30 seconds and 72° C. for 1 minute. At the end of the 25 cycles, the PCR mixture incubated at 72° C. for 5 minutes (37). The PCR products obtained from the target sequences were then sequenced using conventional methods.

Example 9

A Variation on the Method for Enriching for Target Sequence for Sequencing with Two Probes Human gDNA (1 µg) was sheared with a Covaris following the manufacturer's protocol for 500 bp fragments (19). The sheared DNA was add to 25 µl hybridization reaction containing 20 nmol of 3' target isolation probes and 20 nmol of 5' probes, each 50 bases in length and specifying the 3' and 5' ends of 100 targets (38). After hybridization, the hybridized target sequences were captured as described in example 2 (39).

The beads were resuspended in a 50 µl reaction mix containing 1× NEBuffer 4, 2.5 units Exonuclease T and 2.5 µl Exonuclease 1 and incubated for 10 minutes at 37° C. The magnetic beads were washed and resuspended in 50 µl of 1× NEBuffer 2 containing 30 units of RecJf (New England Biolabs, Ipswich, Mass.) and incubated for 10 minutes at 20° C. (FIG. 4).

The magnetic beads were washed and resuspended in 50 µl of dA-Tailing reaction mix and incubated for 30 minutes at 37° C. The beads were then washed and resuspended in 45 µl of 1× Quick Ligation buffer and the NEBNext adaptor for Illumina. 5 µl of Quick T4 DNA ligase was added to the ligation mixture and incubated at room temperature for 15 minutes (41).

USER cleavage of the adaptors and PCR amplification were performed as described in Example 1 (42).

What is claimed is:

1. A method for ligating an adapter to a 3' end of a target sequence in a population of nucleic acids, wherein at least some of the nucleic acids in the population of nucleic acids contain a target sequence and non-target sequences and the non-target sequences comprising a 3' non-target sequence, comprising:
   (a) combining the population of nucleic acids with a target isolation probe in a solution, wherein the target isolation probe comprises an affinity binding domain and is a nucleic acid probe;
   (b) permitting a single stranded region of the target isolation probe to hybridize to all or a portion of a target sequence in the population of nucleic acids, thereby producing hybridized nucleic acids comprising the 3' non-target sequence, wherein the 3' non-target sequence in the hybridized nucleic acids is single stranded;
   (c) enriching the hybridized nucleic acids of step (b) by associating the target isolation probe with a capture domain, thereby producing enriched nucleic acids comprising the hybridized nucleic acids;
   (d) removing the 3' non-target sequence from the enriched nucleic acids of step (c) using one or more 3' single strand specific exonucleases, thereby producing cleaved enriched nucleic acids; and
   (e) ligating an adaptor to the 3' end of the target sequence of the cleaved enriched nucleic acids after the 3' non-target sequence is removed in step (d).

2. The method according to claim 1, wherein some or all of the nucleic acids in the population contains a repeat sequence, and wherein step (a) further comprises combining the population of nucleic acids with a removable blocking oligonucleotide that hybridizes to the repeat sequence.

3. The method according to claim 2, wherein the enriched nucleic acids of step (c) further comprise the removable blocking oligonucleotide and step (d) further comprises selectively degrading the removable blocking oligonucleotide.

4. The method according to claim 1, wherein the single strand region of the target isolation probe in step (b) hybridizes to a first portion of the target sequence.

5. The method according to claim 4, wherein an end of the target isolation probe forms a duplex with a sequence located in or proximate to the 3' end or the 5' end of the target sequence.

6. The method according to claim 4, further comprising, subsequent to step (b), permitting hybridization of a single stranded region of an oligonucleotide probe to a second portion of the target sequence.

7. The method according to claim 6, wherein the second portion of the target sequence is adjacent to, proximate to or distant from the first portion of the target sequence.

8. The method according to claim 7, wherein an end of the oligonucleotide probe forms a duplex with a sequence located in or proximate to the 5' end or 3' end of the target sequence but does not form a duplex with the sequences located in or proximate to both the 5' end and 3' end of the target sequence.

9. The method according to claim 8, wherein the target isolation probe hybridizes to one end of the target sequence and the oligonucleotide probe hybridizes to an opposite end of the target sequence such that hybridization of the target isolation probe and the second probe defines the ends of the target sequence.

10. The method according to claim 6, wherein the target isolation probe or the oligonucleotide probe is a flap probe having: i) a single stranded region that hybridizes to the target sequence, and ii) a double stranded region extending from the 3' end of the single stranded region.

11. The method according to claim 10, wherein the double stranded region of the flap probe comprises a 3'-5' oligonucleotide or the flap probe is a hairpin probe and wherein the method further comprises ligating the 3'-5' oligonucleotide or the hairpin probe to the 5' end of the target sequence.

12. The method according to claim 11, further comprising ligating 3' end of a double stranded region of an adaptor to the 5' end of the target sequence.

13. The method according to claim 4, wherein the affinity binding domain is positioned at the 3' end of the target isolation probe.

14. The method according to claim 4, wherein the affinity binding domain is positioned between the 3' end and the 5' end of the target isolation probe.

15. The method according to claim 4, further comprising hybridizing an oligonucleotide having a random sequence of 4-10 nucleotides to nucleic acids in the population.

16. The method according to claim 1, wherein the non-target sequences further comprise 5' non-target sequence such that both the hybridized nucleic acids and the enriched nucleic acids further comprise the 5' non-target sequence in a single stranded form, the method further comprising removing the 5' non-target sequence from the enriched nucleic acids of step (c) using one or more 5' single strand specific exonucleases.

17. The method according to claim 16, further comprising: ligating an adaptor to each end of the target sequence and sequencing the target sequence.

18. The method according to claim 17, further comprising: detecting a mutation in the target sequence.

19. The method according to claim 18, wherein the mutation is selected from the group consisting of an insertion, deletion, or nucleotide polymorphism.

20. The method according to claim 19, comprising: correlating the mutation in the target sequence with a variation in phenotype of an organism.

21. The method according to claim 1, the adaptor is a hairpin adaptor and step (e) further comprising ligating a duplex region of the hairpin adaptor to the 3' end of the target sequence and the 5' end of the target isolation probe, thereby covalently linking the target isolation probe to the target sequence.

22. The method according to claim 1, further comprising extending the 3' end of the target isolation probe sequence using a polymerase.

23. The method according to claim 1, wherein the single stranded region of the target isolation probe hybridizes to both the 3' end and the 5' end of the target sequence.

24. The method according to claim 23, wherein the affinity binding domain of the target isolation probe is located in a region that is between the 3' end of the target isolation probe and the 5' end of the target isolation probe.

25. The method of claim 23, wherein the non-target sequences further comprise 5' non-target sequence such that both the hybridized nucleic acids and the enriched nucleic acids further comprise the 5' non-target sequence in a single stranded form, the method further comprising removing the 5' non-target sequence from the enriched nucleic acids of step (c) using one or more 5' single strand specific exonucleases.

26. The method according to claim 25, further comprising ligating an adaptor molecule to the 5' end of the target sequence.

27. The method according to claim 26, wherein the adaptor comprises at least one of a sequencing primer site, a library amplification primer site, a unique sample identifier and a unique molecule identifier sequence.

28. A method of obtaining the nucleotide sequence of a target sequence from an extract of an animal or a plant, comprising
(i) obtaining a nucleic acid sample comprising a population of nucleic acids from the extract;
(ii) producing a nucleic acid comprising the target sequence, an adaptor on its 3' end and an adaptor on its 5' end from the population of nucleic acids using the method of claim 26; and
(iii) obtaining the nucleotide sequence of the target sequence from the nucleic acid.

29. The method according to claim 28, further comprising obtaining the nucleotide sequence of the nucleic acid, wherein the nucleotide sequence of the nucleic acid comprises fewer than 5 non-target nucleotides at its 3' end or wherein the nucleotide sequence of the nucleic acid comprises at least 90% of the target sequence.

30. The method according to claim 28, wherein step (ii) further comprises amplifying the nucleic acid using primer sequences that hybridize to sequences positioned within the adaptors located at 3' and 5' ends of the nucleic acid.

31. The method according to claim 28, further comprising correlating features of the target sequence with a phenotype of a prokaryote or eukaryote.

32. The method according to claim 1, wherein the target isolation probe is a flap probe comprising a single stranded region and a double stranded region, and the double stranded region extending from the 3' end of the single stranded region.

33. The method according to claim 1, wherein the population of nucleic acids is derived from a nucleic acid sample obtained from a virus, a prokaryote or a eukaryote.

34. The method according to claim 33, wherein the eukaryote is a plant or an animal.

35. The method according to claim 1, wherein the population of nucleic acids is derived from a eukaryotic nucleic acid sample obtained from a biological sample.

36. The method according to claim 35, wherein the biological sample is a biological fluid.

* * * * *

SEQUENCE LISTING

<160> NUMBER OF SEQ ID NOS: 8

<210> SEQ ID NO 1
<211> LENGTH: 51
<212> TYPE: DNA
<213> ORGANISM: Artificial Sequence -continued

```
<220> FEATURE:
<223> OTHER INFORMATION: Synthetic construct
<220> FEATURE:
<221> NAME/KEY: misc_feature
<222> LOCATION: (35)..(42)
<223> OTHER INFORMATION: n is a, c, g, or t

<400> SEQUENCE: 1
agatcggaag agcacacgtc tgaactccag tcacnnnnnn nnatctcgta t          51

<210> SEQ ID NO 2
<211> LENGTH: 50
<212> TYPE: DNA
<213> ORGANISM: Artificial Sequence
<220> FEATURE:
<223> OTHER INFORMATION: Synthetic construct

<400> SEQUENCE: 2
tctagccttc tcgtgtgcag acttgaggtc agtggttcgt ccttctgccg             50

<210> SEQ ID NO 3
<211> LENGTH: 66
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (35)..(42)
<223> OTHER INFORMATION: n is a, c, g, or t

<400> SEQUENCE: 3
agatcggaag agcacacgtc tgaactccag tcacnnnnnn nnatctcgta tgccgtcttc  60
tgcttg                                                             66

<210> SEQ ID NO 4
<211> LENGTH: 33
<212> TYPE: DNA
<213> ORGANISM: Artificial Sequence
<220> FEATURE:
<223> OTHER INFORMATION: Synthetic construct

<400> SEQUENCE: 4
ctagccttct cgtgtgcaga cttgaggtca gtg                               33

<210> SEQ ID NO 5
<211> LENGTH: 67
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (29)..(34)
<223> OTHER INFORMATION: n is a, c, g, or t

<400> SEQUENCE: 5
atgatacggc gaccaccgag atctacacnn nnnnacactc tttccctaca cgacgctctt  60
ccgatct                                                            67

<210> SEQ ID NO 6
<211> LENGTH: 68
<212> TYPE: DNA
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (30)..(36)
<223> OTHER INFORMATION: n is a, c, g, or t

<400> SEQUENCE: 6
ttactatgcc gctggtggct ctagatgtgn nnnnntgtga gaaagggatg tgctgcgaga      60
aggctaga                                                              68

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
aatgatacgg cgaccaccga                                                 20

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
agcatacggc agaagacgaa c                                               21
```